(12) United States Patent
Enaida et al.

(10) Patent No.: US 7,731,941 B2
(45) Date of Patent: Jun. 8, 2010

(54) STAINING COMPOSITION FOR STAINING AN OPHTHALMIC MEMBRANE

(75) Inventors: Hiroshi Enaida, Fukuoka (JP); Toshio Hisatomi, Fukuoka (JP); Tatsuro Ishibashi, Fukuoka (JP); Tadahisa Kagimoto, Fukuoka (JP); Yasuaki Hata, Fukuoka (JP)

(73) Assignee: National University Corporation Kyushu University, Fukuoka, Fukuoka (JP)

( * ) Notice: Subject to any disclaimer, the term of this patent is extended or adjusted under 35 U.S.C. 154(b) by 95 days.

(21) Appl. No.: 11/792,462

(22) PCT Filed: Dec. 6, 2005

(86) PCT No.: PCT/JP2005/022738

§ 371 (c)(1),
(2), (4) Date: Jun. 6, 2007

(87) PCT Pub. No.: WO2006/062233

PCT Pub. Date: Jun. 15, 2006

(65) Prior Publication Data

US 2008/0090914 A1 Apr. 17, 2008

Related U.S. Application Data

(60) Provisional application No. 60/633,592, filed on Dec. 6, 2004, provisional application No. 60/647,504, filed on Jan. 27, 2005.

(51) Int. Cl.
*A61K 49/00* (2006.01)
*A61K 31/135* (2006.01)
(52) U.S. Cl. ............... 424/10.32; 514/656; 514/912
(58) Field of Classification Search ............ 514/183, 514/656, 912; 424/10.32
See application file for complete search history.

(56) References Cited

U.S. PATENT DOCUMENTS

| | | | |
|---|---|---|---|
| 5,132,439 A * | 7/1992 | Schultz et al. | 552/302 |
| 6,057,160 A | 5/2000 | Silber et al. | |
| 6,367,480 B1 * | 4/2002 | Coroneo | 128/898 |
| 6,372,449 B1 | 4/2002 | Coroneo et al. | |
| 2006/0140863 A1 | 6/2006 | Meinert et al. | |

FOREIGN PATENT DOCUMENTS

| | | |
|---|---|---|
| WO | 2004/035091 A | 4/2004 |
| WO | 2004/035091 A1 | 4/2004 |
| WO | WO-2004/035091 A1 | 4/2004 |

OTHER PUBLICATIONS

Scott E. Burk, ND, PHD, et. al.; "Indocyanine Green—assisted Peeling of the Retinal Internal Limiting Membrane"; Ophthalmology, vol. 107, No. 11, Nov. 2000; pp. 2010-2014 (4 pages).

Alvin K. H. Kwok, MD, FRCS, et. al.; "Indocyanine Green—Assisted Internal Limiting Membrane Removal in Epiretinal Membrane Surgery: a Clinical and Histologic Study"; American Journal of Ophthalmology, vol. 138, No. 2, pp. 194-199. (6 pages).
Vijay K. Dada, MBBS, MS; et al.; "Anterior capsule staining for capsulorhexis in cases of white cataract—Comparative clinical study"; Journal of Cataract and Refractive Surgery, vol. 30, pp. 326-333 (Feb. 2004). (8 pages).
Masayuki Horiguchi, MD, et al.; "Staining of the Lens Capsule for Circular Continuous Capsulorrhexis in Eyes With White Cataract"; Archives of Ophthalmology, vol. 116; pp. 535-537 (Apr. 1998) (3 pages).
Notification of the First Office Action issued May 22, 2009, by The Patent Office of the People's Republic of China, in China Patent Application No. 2005800416779, with English translation (9 pages).
Chi Zhang, et al., "Determination of Protein and Amino Acid Content in Premna"; Journal of Hubei University for Nationalities (Natural Science Edition), 21(1), Mar. 30, 2003; pp. 68-70 (cited in the First Office Action dated May 22, 2009 in China Patent Application No. 2005800416779).
Office Action issued Jun. 9, 2009, by the Canadian Intellectual Property Office, in related-Canadian Patent Application No. 2,590,388 (3 pages) (Please note: The reference, PCT WO 2004/035091, published Apr. 29, 2004, was previously submitted to the USPTO in the IDS filed with the original Application on Jun. 6, 2007.).
EPO Communication of Notice of Opposition filed, issued Feb. 2, 2010, in related Europen Patent Application No. 05814729.9 (2 pages).
EPO Communication of a Notice of Opposition issued Jan. 22, 2010, by the European Patent Office, in related European Patent Application No. 05814729.9, together with the Notice of Opposition filed by Fluoron GmbH, and the English translation of the Notice of Opposition (14 pages).
Tal, Moshe, et al., "Why Does Coomassie Brilliant Blue R Interact Differently with Different Proteins?"; The Journal of Biological Chemistry, ASBMB, vol. 260, No. 18, (Aug. 25, 1980); pp. 9976-9980.
Smejkal, Gary B., "The Coomassie chronicles: past, present and future perspectives in polyacrylamide gel staining"; Future Drugs Ltd. (2004); Expert Rev. Proteoinics 1(4), (2004); ISSN 1478-9450; pp. 381-386.
Diezel, W., et al., "An Improved Procedure for Protein Staining in Polyacrylamide Gels with a New Type of Coomassie Brilliant Blue"; Analytical Biochemistry 48 (1972); pp. 617-620.
Russell, Stephen R., et al., "Distribution of Glycoconjugates in the Human Retinal Internal Limiting Membrane"; Investigative Ophthalmology & Visual Science, vol. 32, No. 7, Jun. 1991; pp. 1986-1995.
Duhamel RC., Abstract of "Differential staining of collagens and non-collagens with Coomassie Brilliant Blue G and R."; Coll Relat Res. 1983; PubMed, U.S. National Library of Medicine, National Institutes of Health (1 page).

* cited by examiner

*Primary Examiner*—Frederick Krass
*Assistant Examiner*—Sara E Clark
(74) *Attorney, Agent, or Firm*—Osha • Liang LLP

(57) ABSTRACT

A staining composition for staining an ophthalmic membrane when performing the ophthalmic membrane removal, wherein the staining composition comprises a Brilliant Blue G (BBG) derivative as a primary component.

6 Claims, 14 Drawing Sheets

STAINING COMPOSITION FOR STAINING AN OPHTHALMIC MEMBRANE

PRIORITY FILING

This application claims priority to U.S. Provisional Application Nos. 60/633,592 filed on Dec. 6, 2004, and 60/647,504 filed on Jan. 27, 2005, the contents of which are incorporated herein by reference in their entirety.

FIELD OF THE INVENTION

The present invention relates to a staining composition for staining an ophthalmic membrane. More specifically, the present invention relates to the staining composition used as an adjuvant for staining the ophthalmic membrane specifically to remove the membrane.

BACKGROUND OF THE INVENTION

The staining of the internal limiting membrane (ILM) is one of the important developments of surgery for such vitreoretinal diseases as macular hole and epiretinal membranes (ERMS) (Indocyanine green-assisted peeling of the retinal internal limiting membrane. Burk S E et al. Opthalmology. 2000; 107:2010-2014). It is now widely recognized that without surgical adjuvant it is extremely difficult to remove the membranes due to the poor visibility of the ILM and ERMS. In particular, Indocyanine green (ICG) and Trypan Blue (TB) staining have greatly facilitated ILM and ERMS peeling in various vitreo-retinal diseases and as a result, this technique is now widely accepted by many surgeons However, numerous reports have recently emerged regarding retinal damage caused by intravitreal injections of ICG and TB both in experimental and clinical use. (Morphological and functional damage of the retina caused by intravitreous indocyanine green in rat eyes. Enaida H, et al. Graefes Arch Clin Exp Opthalmol. 2002; 240:209-213; Uemura A, et al. Visual field defects after uneventful vitrectomy for epiretinal membrane with indocyanine green-assisted internal limiting membrane peeling. Am J Opthalmol. 2003; 136:252-257; Veckeneer M, et al. Ocular toxicity study of trypan blue injected into the vitreous cavity of rabbit eyes. Graefes Arch Clin Exp Opthalmol. 2001; 239:698-704).

Further, creating a continuous curvilinear capsulorhexis (CCC) in eyes with a white mature cataract can be challenging as it is difficult to distinguish the anterior capsule from the underlying white cortex. Poor visualization of the capsule tends to result in an incomplete or inadequate CCC that could cause a subsequent capsular tear, vitreous loss and intraocular lens (IOL) dislocation. The intraocular administration of dyes for anterior capsule staining to perform CCC in eyes with a cataract with poor or no red reflex has become increasingly popular. Dada demonstrated that capsular staining facilitates the CCC even in immature cataracts and could be a useful adjunct for trainee surgeons. Trypan blue 0.1% and 0.06% have been introduced to capsular staining, and has been found to have no apparent toxicity in vivo. However, trypan blue has been reported to be toxic to corneal endothelium in vitro in severe conditions. Indocyanine green (ICG) is also a frequently used dye for capsular staining. McEnerney and Peyman described the use of ICG for cell counts in rabbit corneal endothelium, and suggested the dye did not damage living endothelium. However, the inventors reported the potential toxicity of ICG to retinal cells in 2002, and recently, the toxicity of ICG has been reported in retinal pigment epithelium, ganglion cells, and photoreceptors. (Indocyanine green induces apoptosis in human retinal pigment epithelial cells. Rezai K A, et al. Am J Opthalmol. 2004; 137:931-933; Trypan blue induces apoptosis in human retinal pigment epithelial cells. Rezai K A et al. Am J Opthalmol. 2004; 138:492-495).

As stated above, dyes (such as IC or TB) conventionally used for staining an ophthalmic membrane, particularly the internal limiting membrane and the anterior capsule have produced questions regarding their safety. Such doubts developed due to reports of the possibility of toxicity, teratogenicity and so on to the retinal cells. Furthermore, there were technical problems such as the inability to get a satisfactory dye at lower concentrations and complicated staining methods. Thus, such problems made ophthalmic surgery an even more difficult matter.

Accordingly, to promote the improvement of ophthalmic surgeries, the development of a dye that specifically colors an ophthalmic membrane, and has the objectives of high staining at low concentrations along with high levels of safety, has been greatly desired.

SUMMARY OF THE INVENTION

Therefore, it is an objective of the present invention to provide a staining composition that is an alternative to dyes conventionally used for staining an ophthalmic membrane. A more detailed objective is to provide a staining composition specifically for staining an internal limiting membrane or an anterior capsule, which is usable as an adjuvant to a surgery for the removal of such a membrane.

In order to provide a staining composition for achieving such objectives, all dyes, including dyes currently not being utilized for organisms were used, and they were then screened for candidate dyes. Additionally, as the screening conditions, safety and staining-affinity were especially noted. Safety assessments were then conducted, using rats, of the narrowed down candidate dyes. Based on higher staining-affinity and safety, Brilliant Blue G (BBG) became the final candidate.

Further, in order to examine the optimal conditions of a staining composition containing BBG for staining an ophthalmic membrane, various experiments were performed. In that way, the staining composition of the present invention was achieved. It should be noted that BBG had not yet been used clinically, especially with regard to human. However, via the optimal conditions for the present invention, a staining composition that is safe for clinical use, and that also has a high staining-affinity, can be provided.

Therefore, according to the first main aspect of the present invention, a staining composition is provided having BBG as a principal component, for staining an ophthalmic membrane at the time of removal of the ophthalmic membrane.

That is, one aspect of the present invention directs to a staining composition for staining an ophthalmic membrane when performing the ophthalmic membrane removal, wherein the staining composition comprises a Brilliant Blue G (BBG) derivative, a pharmaceutically acceptable salt thereof or a hydrate thereof, as a primary component.

The preferred BBG derivative is represented by formula [I],

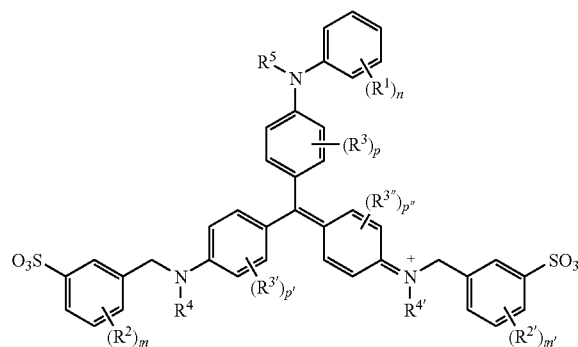

wherein, $R^1$ represents a $C_{1-10}$alkoxy group, a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a hydroxy$C_{2-10}$alkyl group, a halogeno$C_{1-10}$alkoxy group, or a halogeno$C_{1-10}$alkyl group, n represents any one of 1 to 5, $R^2$ and $R^{2'}$ are identical or different, and each represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy$C_{2-10}$alkyl group, or a halogeno$C_{1-10}$alkyl group, m and m' are identical or different, and each represents any one of 1 to 4, $R^3$, $R^{3'}$ and $R^{3''}$ are identical or different, and each represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy$C_{2-10}$alkyl group, or a halogeno$C_{1-10}$alkyl group, p, p' and p" are identical or different, and each represents any one of 1 to 4, $R^4$ and $R^{4'}$ are identical or different, and each represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy$C_{2-10}$alkyl group, or a halogeno$C_{1-10}$alkyl group, and $R^5$ represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy$C_{2-10}$alkyl group, or a halogeno$C_{1-10}$alkyl group.

The further preferred BBG derivative represented by formula [I] is, $R^1$ represents a $C_{1-6}$alkoxy group, a hydrogen atom, —OH, a $C_{1-6}$alkyl group, a $C_{2-6}$alkenyl group, a $C_{2-6}$alkynyl group, a $C_{1-6}$alkyl group substituted by one or two aryl groups, a hydroxy$C_{2-6}$alkyl group, a halogeno$C_{1-6}$alkoxy group, or a halogeno$C_{1-6}$alkyl group, n represents any one of 1 to 5, $R^2$ and $R^{2'}$ are identical or different, and each represents a hydrogen atom, —OH, a $C_{1-6}$alkyl group, a $C_{2-6}$alkenyl group, a $C_{2-6}$alkynyl group, a $C_{1-6}$alkyl group substituted by one or two aryl groups, a $C_{1-6}$alkoxy group, a hydroxy $C_{2-6}$alkyl group, or a halogeno$C_{1-6}$alkyl group, m and m' are identical or different, and each represents any one of 1 to 4, $R^3$, $R^{3'}$ and $R^{3''}$ are identical or different, and each represents a hydrogen atom, —OH, a $C_{1-6}$alkyl group, a $C_{2-6}$alkenyl group, a $C_{2-6}$alkynyl group, a $C_{1-6}$alkyl group substituted by one or two aryl groups, a $C_{1-6}$alkoxy group, a hydroxy $C_{2-6}$alkyl group, or a halogeno$C_{1-6}$alkyl group, p, p' and p" are identical or different, and each represents any one of 1 to 4, $R^4$ and $R^{4'}$ are identical or different, and each represents a hydrogen atom, —OH, a $C_{1-6}$alkyl group, a $C_{2-6}$alkenyl group, a $C_{2-6}$alkynyl group, a $C_{1-6}$alkyl group substituted by one or two aryl groups, a $C_{1-6}$alkoxy group, a hydroxy $C_{2-6}$alkyl group, or a halogeno$C_{1-6}$alkyl group, and $R^5$ represents a hydrogen atom, —OH, a $C_{1-6}$alkyl group, a $C_{2-6}$alkenyl group, a $C_{2-6}$alkynyl group, a $C_{1-6}$alkyl group substituted by one or two aryl groups, a $C_{1-6}$alkoxy group, a hydroxy$C_{2-6}$alkyl group, or a halogeno$C_{1-6}$alkyl group.

The preferred BBG derivative is represented by formula [II],

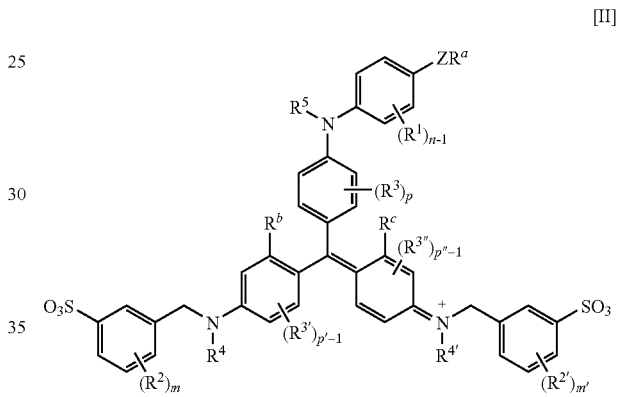

wherein, $R^1$ represents a hydrogen atom, —OH, a $C_{1-6}$alkyl group, a hydroxy$C_{2-6}$alkyl group, or a halogeno$C_{1-6}$alkyl group, n represents any one of 1 to 5, Z represents —O—, —S—, —N=, —OC(=O)—, or —C(=O)O—, $R^a$ represents a hydrogen atom, —OH, a $C_{1-6}$alkyl group, a hydroxy$C_{2-6}$alkyl group, or a halogeno$C_{1-6}$alkyl group, $R^2$ and $R^{2'}$ are identical or different, and each represents a hydrogen atom, —OH, a $C_{1-6}$alkyl group, $C_{1-6}$alkoxy group, a hydroxy$C_{2-6}$alkyl group, a halogeno$C_{1-6}$alkyl group, m and m' are identical or different, and each represents any one of 1 to 4, $R^3$, $R^{3'}$ and $R^{3''}$ are identical or different, and each represents a hydrogen atom, —OH, a $C_{1-6}$alkyl group, a $C_{1-6}$alkoxy group, a hydroxy$C_{2-6}$alkyl group, or a halogeno$C_{1-6}$alkyl group, p, p' and p" are identical or different, and each represents any one of 1 to 4, $R^b$ and $R^c$ are identical or different, and each represents a $C_{1-6}$alkyl group, a $C_{1-6}$alkoxy group, a hydroxy$C_{2-6}$alkyl group, or a halogeno$C_{1-6}$alkyl group, $R^4$ and $R^{4'}$ are identical or different, and each represents a hydrogen atom, or a $C_{1-6}$alkyl group, and $R^5$ represents a hydrogen atom, a $C_{1-6}$alkyl group, or a halogeno$C_{1-6}$alkyl group.

It is preferred that in formula [II],
$R^1$ represents a hydrogen atom, or a $C_{1-6}$alkyl group,
n represents any one of 1 to 5,
Z represents —O—,
$R^a$ represents a $C_{1-6}$alkyl group,
$R^2$ and $R^{2'}$ are identical or different, and each represents a hydrogen atom, or a $C_{1-6}$alkyl group,
m and m' are identical or different, and each represents any one of 1 to 4,
$R^3$, $R^{3'}$ and $R^{3''}$ represent a hydrogen atom,
p, p' and p'' represent 4,
$R^b$ and $R^c$ are identical or different, and each represents a $C_{1-6}$alkyl group,
$R^4$ and $R^{4'}$ are identical or different, and each represents a $C_{1-6}$alkyl group, and
$R^5$ represents a hydrogen atom, a $C_{1-6}$alkyl group.

The preferred BBG derivative is represented by formula [III],

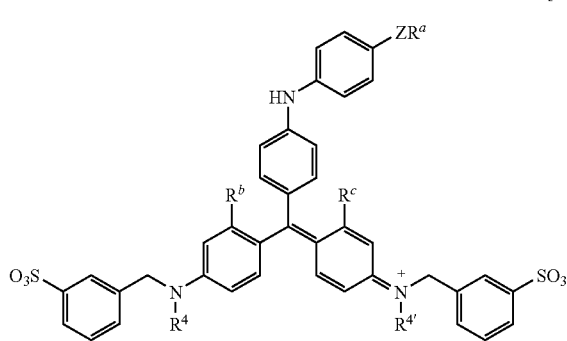

[III]

wherein,
Z represents —O—, —S—, —N=, —OC(=O)—, or —C(=O)O—,
$R^a$ represents a hydrogen atom, —OH, a $C_{1-6}$alkyl group, a hydroxy$C_{2-6}$alkyl group, or a halogeno$C_{1-6}$alkyl group,
$R^b$ and $R^c$ are identical or different, and each represents a $C_{1-6}$alkyl group, a $C_{1-6}$alkoxy group, a hydroxy$C_{2-6}$alkyl group, or a halogeno$C_{1-6}$alkyl group, and
$R^4$ and $R^{4'}$ are identical or different, and each represents a hydrogen atom, or a $C_{1-6}$alkyl group.

It is preferred that in formula [III],
Z represents —O—,
$R^a$ represents a $C_{1-6}$alkyl group, or a halogeno$C_{1-6}$alkyl group,
$R^b$ and $R^c$ are identical or different, and each represents a $C_{1-6}$alkyl group, or a halogeno$C_{1-6}$alkyl group, and
$R^4$ and $R^{4'}$ are identical or different, and each represents a $C_{1-6}$alkyl group.

It is preferred that in formula [III],
Z represents —O—,
$R^a$ represents a $C_{1-3}$alkyl group,
$R^b$ and $R^c$ are identical or different, and each represents a $C_{1-3}$alkyl group, and
$R^4$ and $R^{4'}$ are identical or different, and each represents a $C_{1-3}$alkyl group.

A further preferred the BBG derivative, a pharmaceutically acceptable salt thereof or a hydrate thereof is a BBG dye.

The $C_{1-10}$alkyl group means a straight-chain alkyl group having one to ten carbon atoms, a branched chain alkyl group having three to ten carbon atoms or a cyclic alkyl group having three to ten carbon atoms. Examples of the straight-chain alkyl group include a methyl group, an ethyl group, a propyl group, a butyl group, a pentyl group, a hexyl group, a heptyl group, an octyl group, a nonyl group and a decyl group. Examples of the branched chain alkyl group include an iso-propyl group, an isobutyl group, a 1-methylpropyl group, a t-butyl group, a 1-methylbutyl group, a 2-methylbutyl group, a 3-methylbutyl group, a 1-ethylpropyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 5-methylhexyl group, a 3-ethylpentyl group, a 1-propylbutyl group, a 1,4-dimethylpentyl group, a 3,4-dimethylpentyl group, a 1,2,3-trimethylbutyl group, a 1-isopropylbutyl group, a 4,4-dimethylpentyl group, a 5-methylheptyl group, a 6-methylheptyl group, a 4-ethylhexyl group, a 2-propylpentyl group, a 2,5-dimethylhexyl group, a 4,5-dimethylhexyl group, a 2-ethyl-3-methylpentyl group, a 1,2,4-trimethylpentyl group, a 2-methyl-1-isopropylbutyl group, a 3-methyloctyl group, a 2,5-dimethylheptyl group, a 1-(1-methylpropyl)-2-methylbutyl group, a 1,4,5-trimethylhexyl group, a 1,2,3,4-tetramethylpentyl group, a 7-methyloctyl group, a 6-methylnonyl group, a 8-methylnonyl group, a 5-ethyl-2-methylheptyl group, a 2,3-dimethyl-1-(1-methylpropyl)butyl group, a cyclopropylmethyl group, a 2-(cyclopropyl)ethyl group, a 3,7-dimethyloctyl group, a 3-(cyclobutyl)pentyl group, a cyclopentylmethyl group and a cyclohexylmethyl group. Examples of the cyclic alkyl group include a cyclopropyl group, a cyclobutyl group, a cyclopentyl group, a cyclohexyl group, a cycloheptyl group and a cyclooctyl group. In the $C_{1-10}$alkyl group, a $C_{1-6}$alkyl group is preferred, and a $C_{1-13}$alkyl group is further preferred.

The $C_{2-10}$alkenyl group means a straight-chain alkenyl group having two to ten carbon atoms with at least one double bond, a branched chain alkenyl group having three to ten carbon atoms or a cyclic alkenyl group having five to ten carbon atoms, examples of which include a vinyl group, an allyl group, a 3-butenyl group, a 4-pentenyl group, a 5-hexenyl group, a 6-heptenyl group, a 7-octenyl group, a 8-nonenyl group, a 9-decenyl group, a 1-methyl-2-butenyl group, a 2-methyl-2-butenyl group, a 2-methyl-3-butenyl group, a 2-pentenyl group, a 2-methyl-2-hexenyl group and a 2-cyclopentenyl group. In the $C_{2-10}$alkenyl group, a $C_{2-6}$alkenyl group is preferred, and a $C_{2-3}$alkenyl group is further preferred.

The $C_{2-10}$alkynyl group means a straight-chain alkynyl group having two to ten carbon atoms with at least one triple bond or a branched chain alkynyl group having four to ten carbon atom, examples of which include a 2-propynyl group, a 3-butynyl group, a 4-pentynyl group, a 5-hexynyl group, a 6-heptynyl group, a 7-octynyl group, a 8-nonynyl group, a 9-decinyl group, a 3-pentynyl group and a 4-methyl-2-pentynyl group. In the $C_{2-10}$alkynyl group, a $C_{2-6}$ alkynyl group is preferred, and a $C_{2-3}$alkynyl group is further preferred.

The $C_{1-10}$alkyl group substituted by one or two aryl groups means, for example, a benzyl group, a diphenylmethyl group, a 2-phenyethyl group, a 2-phenylpropyl group, a 1-methyl-1-phenyethyl group, a 1-methyl-2-phenylpentyl group, a 2-nitrobenzyl group, a 3-nitrobenzyl group, a 4-nitrobenzyl group, a 2,4-dinitrobenzyl group, a 2,4,6-trinitrobenzyl group, a 2-phenylbenzyl group, a 3-phenylbenzyl group, a 4-phenylbenzyl group, a 2-hydroxybenzyl group, a 3-hydroxybenzyl group, a 4-hydroxybenzyl group, a 2-chlorobenzyl group, a 3-chlorobenzyl group, a 4-chlorobenzyl group, a 2-fluorobenzyl group, a 3-fluorobenzyl group, a 4-fluorobenzyl group, a 2-beromobenzyl group, a 3-beromobenzyl group, a 4-beromobenzyl group, a 2-iodobenzyl group, a 2-iodobenzyl group, a 2,3-dichlorobenzyl group, a 2,4-dichlorobenzyl group, a 2,5-dichlorobenzyl group, a 2,6-dichlorobenzyl group, a 3,4-dichlorobenzyl group, a 3,5-dichlorobenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-isopropylbenzyl group, a 3-isopropylbenzyl group, a 4-isopropylbenzyl group, a 2-methoxybenzyl group, a 3-methoxybenzyl group, a 4-methoxybenzyl group, a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, a 3,5-dimethoxybenzyl group, a 2-ethoxybenzyl group, a 3-ethoxybenzyl group, a 4-ethoxybenzyl group, a 2-isopropoxybenzyl group, a 3-isopropoxybenzyl group, a 4-isopropoxybenzyl group, a 2-methoxymethylbenzyl group, a 3-methoxymethylbenzyl group, a 4-methoxymethylbenzyl group, a 2-isopropyxymethylbenzyl group, a 3-isopropyxymethylbenzyl group, a 4-isopropyxymethylbenzyl group, a 2-trifluoromethyl group, a 3-trifluoromethyl group, a 4-trifluoromethyl group, a 2-hydroxycarbonylbenzyl group, a 3-hydroxycarbonylbenzyl group, a 4-hydroxycarbonylbenzyl group, a 2-aminobenzyl group, a 3-aminobenzyl group, a 4-aminobenzyl group, a 2-aminomethylbenzyl group, a 3-aminomethylbenzyl group, a 4-aminomethylbenzyl group, a 2-cyanobenzyl group, a 3-cyanobenzyl group, a 4-cyanobenzyl group, a 2-hydroxymethylbenzyl group, a 3-hydroxymethylbenzyl group, a 4-hydroxymethylbenzyl group, a 2-phenoxybenzyl group, a 3-phenoxybenzyl group and a 4-phenoxybenzyl group. As the $C_{1-10}$alkyl group of the $C_{1-10}$alkyl group of substituted by one or two aryl groups, a $C_{1-6}$alkyl group is preferred, and a $C_{1-3}$alkyl group is further preferred.

The aryl group means a phenyl group, a substituted phenyl group or a polycyclic aromatic group such as a 1-naphthyl group or a 2-naphthyl group.

The hydroxy$C_{2-10}$alkyl group means a $C_{2-10}$alkyl group substituted by at least one hydroxyl group, examples of which include a 2-hydroxyethyl group, a 3-hydroxypropyl group, a 4-hydroxybutyl group, a 5-hydroxypentyl group, a 6-hydroxyhexyl group, a 7-hydroxyheptyl group, a 8-hydroxyoctyl group, a 9-hydroxynonyl group, a 10-hydroxydecyl group, a 2-hydroxypropyl group, a 2,3-dihydroxypropyl group and a 2-hydroxy-3-methylbutyl group. In the hydroxy$C_{2-10}$alkyl group, a hydroxy$C_{2-6}$alkyl group is preferred, and a hydroxy$C_{2-3}$alkyl group is further preferred.

The halogeno$C_{1-10}$alkyl group means a $C_{1-10}$alkyl group substituted by at least one fluorine atom, chlorine atom, bromine atom or iodine atom, examples of which include a 2-chloroethyl group, a 2-bromoethyl group, a 2-iodoethyl group, a 3-chloropropyl group, a 3-bromopropyl group, a 3-iodopropyl group, a 4-chlorobutyl group, a 4-bromobutyl group, a 4-iodobutyl group, a 5-chloropentyl group, a 6-chlorohexyl group, a 7-chloroheptyl group, a 8-chlorooctyl group, a 9-chlorononyl group, a 10-chlorodecyl group, a 2-chloropropyl group, a 2-chlorobutyl group, a 2,4-dichlorobutyl group and a 2-chloro-3-methylbutyl group. In the halogeno$C_{1-10}$alkyl group, a halogeno$C_{1-6}$alkyl group is preferred, and a halogeno$C_{1-10}$alkyl group is further preferred.

The $C_{1-10}$alkoxy$C_{1-10}$alkyl group means a alkyl group having one to ten carbons which is substituted by a straight-chain alkoxy group having one to ten carbons, a branched chain alkoxy group having three to ten carbon atoms or a cyclic alkoxy group having three to ten carbon atoms, examples of which include a 2-methoxyethyl group, a 2-ethoxyethyl group, a 2-propoxyethyl group, a 2-isopropoxyethyl group, a 2-butoxyethyl group, a 2-isobutoxyethyl group, a 2-t-butoxyethyl group, a 2-pentyloxyethyl group, a 2-hexenyloxyethyl group, a 3-ethoxypropyl group, a 4-ethoxybutyl group, a 4-ethoxy-3-methoxybutyl group and a 4-ethoxy-3-methylpentyl group. In the $C_{1-10}$alkoxy$C_{1-10}$alkyl group, a $C_{1-6}$alkoxy$C_{1-6}$alkyl group is preferred, and a $C_{1-3}$alkoxy $C_{1-3}$alkyl group is further preferred.

The halogeno$C_{1-10}$alkoxy group means a $C_{1-10}$alkoxy group substituted by at least one fluorine atom, chlorine atom, bromine atom or iodine atom. In the halogeno$C_{1-10}$alkoxy group, a halogeno$C_{1-6}$alkoxy group is preferred, and a halogeno$C_{1-3}$alkoxy group is further preferred.

The preferred stereostructure of the BBG derivative of the present invention is optically active bodies having the absolute structure, but the BBG derivative of the present invention may be present as enantiomers or enantiomer mixtures such as racemic bodies. Therefore, the BBG derivative of the present invention includes all of the optically active bodies, the enantiomer mixtures such as racemic bodies and the diastereomer mixtures of the BBG derivative represented by the above formula [I].

Examples of the pharmaceutically acceptable salt includes salts formed with inorganic bases, ammonia, organic bases, inorganic acids, organic acids, basic amino acids, halogen ions or the like, and inner molecular salts. Examples of the inorganic base include alkaline metal (e.g., Na, K) and alkaline earth metal (e.g., Ca, Mg). Examples of the organic base include trimethylamine, triethylamine, choline, procaine, ethanolamine and the like. Examples of the inorganic acid include hydrochloric acid, hydrobromic acid, sulfuric acid, nitric acid, and phosphoric acid and the like. Examples of the organic acid include p-toluene sulfonic acid, methanesulfonic acid, formic acid, trifluoroacetic acid and maleic acid and the like. Examples of the basic amino acid include lysine, arginine, ornithine, histidine and the like. The compound may be a pharmaceutically acceptable hydrate.

According to one preferred embodiment of the present invention, said staining composition can be used as a surgical adjuvant in ophthalmic surgeries related to ophthalmic diseases, such as, for example, vitreo-retinal disease such as Macular hole, retinal detachment due to hymyopic macular hole, epiretinal membrane, proliferative diabetic retinopathy, diabetic macular edema, and proliferative vitreoretinopathy, and specific cataracts such as hypermature cataract, and congenital cataract, and split-thickness corneal transplantation, etc. According to the staining composition of the present invention, it becomes possible to more clearly verify difficult-to-see ophthalmic membranes, and improve safety during surgical operations.

In a further preferred embodiment of the present invention, said staining composition can be used for staining an ophthalmic membrane and, more preferably, for staining the internal limiting membrane and/or the anterior capsule.

In one preferred embodiment of the present invention, it is desirable that the staining composition of the present invention contain BBG derivative at a concentration of 0.1-10 mg/ml, preferably a concentration of 0.1-1.0 mg/ml, and most preferably a concentration of 0.1-0.25 mg/ml. In this embodiment, a staining composition having a high staining-affinity at low concentrations and small quantities is provided.

Furthermore, it is preferable according to the one embodiment of the present invention for the staining composition to have an osmotic pressure in the environs of 298 mOsm. According to this embodiment, the staining composition of the present invention has an osmotic pressure equal to a physiological saline. Thus, any problems occurring due to differences in osmotic pressure are neutralized.

In one preferred embodiment of the present invention, it is desirable that the staining composition of the present invention displays a neutral pH, that is, a pH in the vicinity of pH=7.4.

According to the second main aspect of the present invention, a method for staining and removing an ophthalmic membrane is provided having the steps of preparing a staining composition having BBG derivative as a principal component; staining the ophthalmic membrane using a predetermined concentration of said staining composition; and removing the stained ophthalmic membrane.

In one preferred embodiment of the present invention, said ophthalmic membrane is an internal limiting membrane and/or an anterior capsule, although it is not necessarily limited to such.

According to the third main aspect of the present invention, a use of BBG derivative in the manufacture of a staining composition for the treatment of ophthalmic diseases is provided.

Furthermore, according to the fourth main aspect of the present invention, a use of BBG derivative as a surgical adjuvant for ophthalmic surgeries is provided.

The materials, methods, and examples provided herein are illustrative only and are not intended to be limiting. Other features and advantages of the invention will be apparent from the following detailed description and claims.

DETAILED DESCRIPTION OF THE INVENTION

Figure 1:
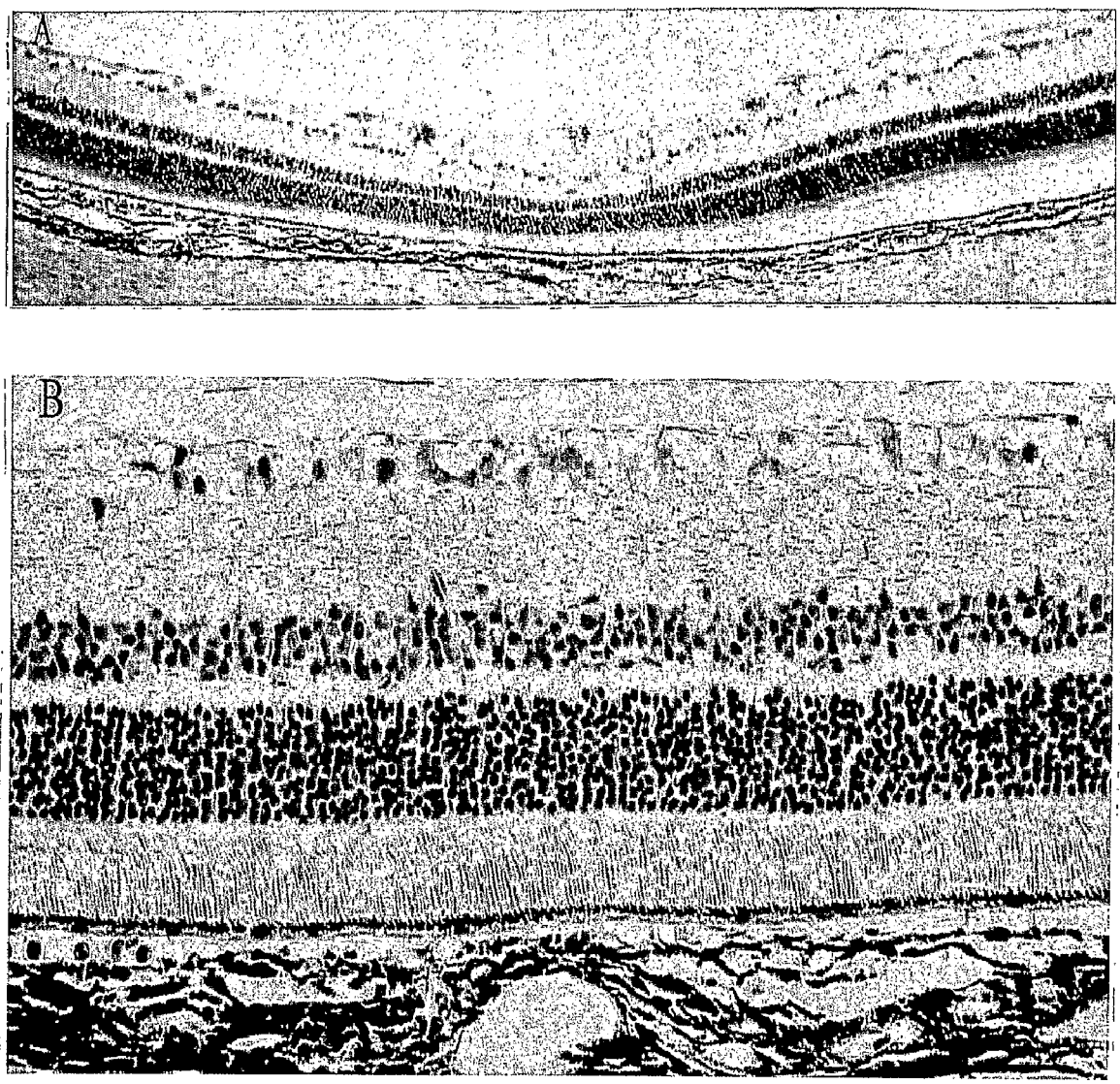
FIG. 1 shows light microscopic photography of rat eyes injected with intravitreal BBG (10 mg/ml, 0.05 ml/eye) visualized at 14 days. (Original magnification A: ×200, B: ×400)

As previously described, an assessment was focused on providing a dye for staining an ophthalmic membrane, as an alternative to dyes conventionally being used such as ICG or TB. Thus, as follows, a number of characteristics were combined, and a staining composition was achieved having a high staining-affinity and a high level of safety.

One aspect of the present invention directs to a staining composition for staining an ophthalmic membrane when performing the ophthalmic membrane removal, wherein the staining composition comprises a Brilliant Blue G (BBG) derivative, a pharmaceutically acceptable salt thereof or a hydrate thereof, as a primary component.

The preferred BBG derivative is represented by formula [I],

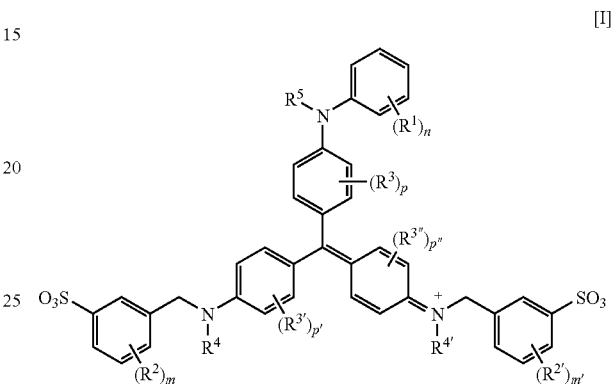

wherein, $R^1$ represents a $C_{1-10}$alkoxy group, a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a hydroxy$C_{2-10}$alkyl group, a halogeno$C_{1-10}$alkoxy group, or a halogeno$C_{1-10}$alkyl group, n represents any one of 1 to 5, $R^2$ and $R^{2'}$ are identical or different, and each represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy $C_{2-10}$alkyl group, or a halogeno$C_{1-10}$alkyl group, m and m' are identical or different, and each represents any one of 1 to 4, $R^3$, $R^{3'}$ and $R^{3''}$ are identical or different, and each represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy$C_{2-10}$alkyl group, or a halogeno$C_{1-10}$alkyl group, p, p' and p'' are identical or different, and each represents any one of 1 to 4, $R^4$ and $R^{4'}$ are identical or different, and each represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy $C_{2-10}$alkyl group, or a halogeno$C_{1-10}$alkyl group, and $R^5$ represents a hydrogen atom, —OH, a $C_{1-10}$alkyl group, a $C_{2-10}$alkenyl group, a $C_{2-10}$alkynyl group, a $C_{1-10}$alkyl group substituted by one or two aryl groups, a $C_{1-10}$alkoxy group, a hydroxy$C_{2-10}$alkyl group, or a halogeno$C_{1-10}$alkyl group.

The further preferred BBG derivative represented by formula [I] is, $R^1$ represents a $C_{1-6}$alkoxy group, a hydrogen atom, —OH, a $C_{1-6}$alkyl group, a $C_{2-6}$alkenyl group, a $C_{2-6}$alkynyl group, a C$_{1-6}$alkyl group substituted by one or two aryl groups, a hydroxyC$_{2-6}$alkyl group, a halogenoC$_{1-6}$alkoxy group, or a halogenoC$_{1-6}$alkyl group, n represents any one of 1 to 5, R$^2$ and R$^{2'}$ are identical or different, and each represents a hydrogen atom, —OH, a C$_{1-6}$alkyl group, a C$_{2-6}$alkenyl group, a C$_{2-6}$alkynyl group, a C$_{1-6}$alkyl group substituted by one or two aryl groups, a C$_{1-6}$alkoxy group, a hydroxy C$_{2-6}$alkyl group, or a halogenoC$_{1-6}$alkyl group, m and m' are identical or different, and each represents any one of 1 to 4, R$^3$, R$^{3'}$ and R$^{3''}$ are identical or different, and each represents a hydrogen atom, —OH, a C$_{1-6}$alkyl group, a C$_{2-6}$alkenyl group, a C$_{2-6}$alkynyl group, a C$_{1-6}$alkyl group substituted by one or two aryl groups, a C$_{1-6}$alkoxy group, a hydroxy C$_{2-6}$alkyl group, or a halogenoC$_{1-6}$alkyl group, p, p' and p'' are identical or different, and each represents any one of 1 to 4, R$^4$ and R$^{4'}$ are identical or different, and each represents a hydrogen atom, —OH, a C$_{1-6}$alkyl group, a C$_{2-6}$alkenyl group, a C$_{2-6}$alkynyl group, a C$_{1-6}$alkyl group substituted by one or two aryl groups, a C$_{1-6}$alkoxy group, a hydroxy C$_{2-6}$alkyl group, or a halogenoC$_{1-6}$alkyl group, and R$^5$ represents a hydrogen atom, —OH, a C$_{1-6}$alkyl group, a C$_{2-6}$alkenyl group, a C$_{2-6}$alkynyl group, a C$_{1-6}$alkyl group substituted by one or two aryl groups, a C$_{1-6}$alkoxy group, a hydroxyC$_{2-6}$alkyl group, or a halogenoC$_{1-6}$alkyl group.

The preferred BBG derivative is represented by formula [II],

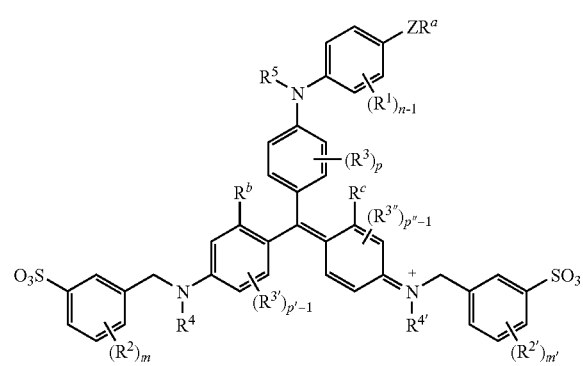

[II]

wherein,

R$^1$ represents a hydrogen atom, —OH, a C$_{1-6}$alkyl group, a hydroxyC$_{2-6}$alkyl group, or a halogenoC$_{1-6}$alkyl group, n represents any one of 1 to 5, Z represents —O—, —S—, —N═, —OC(═O)—, or —C(═O)O—, R$^a$ represents a hydrogen atom, —OH, a C$_{1-6}$alkyl group, a hydroxyC$_{2-6}$alkyl group, or a halogenoC$_{1-6}$alkyl group, R$^2$ and R$^{2'}$ are identical or different, and each represents a hydrogen atom, —OH, a C$_{1-6}$alkyl group, C$_{1-6}$alkoxy group, a hydroxyC$_{2-6}$alkyl group, a halogenoC$_{1-6}$alkyl group, m and m' are identical or different, and each represents any one of 1 to 4, R$^3$, R$^{3'}$ and R$^{3''}$ are identical or different, and each represents a hydrogen atom, —OH, a C$_{1-6}$alkyl group, a C$_{1-6}$alkoxy group, a hydroxyC$_{2-6}$alkyl group, or a halogenoC$_{1-6}$alkyl group, p, p' and p'' are identical or different, and each represents any one of 1 to 4, R$^b$ and R$^c$ are identical or different, and each represents a C$_{1-6}$alkyl group, a C$_{1-6}$alkoxy group, a hydroxyC$_{2-6}$alkyl group, or a halogenoC$_{1-6}$alkyl group, R$^4$ and R$^{4'}$ are identical or different, and each represents a hydrogen atom, or a C$_{1-6}$alkyl group, and R$^5$ represents a hydrogen atom, a C$_{1-6}$alkyl group, or a halogenoC$_{1-6}$alkyl group.

It is preferred that in formula [II],

R$^1$ represents a hydrogen atom, or a C$_{1-6}$alkyl group, n represents any one of 1 to 5, Z represents —O—, R$^a$ represents a C$_{1-6}$alkyl group, R$^2$ and R$^{2'}$ are identical or different, and each represents a hydrogen atom, or a C$_{1-6}$alkyl group, m and m' are identical or different, and each represents any one of 1 to 4, R$^3$, R$^{3'}$ and R$^{3''}$ represent a hydrogen atom, p, p' and p'' represent 4, R$^b$ and R$^c$ are identical or different, and each represents a C$_{1-6}$alkyl group, R$^4$ and R$^{4'}$ are identical or different, and each represents a C$_{1-6}$alkyl group, and R$^5$ represents a hydrogen atom, a C$_{1-6}$alkyl group.

The preferred BBG derivative is represented by formula [III],

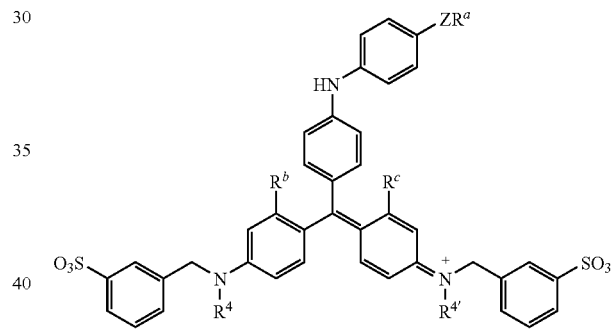

[III]

wherein,

Z represents —O—, —S—, —N═, —OC(═O)—, or —C(═O)O—,

R$^a$ represents a hydrogen atom, —OH, a C$_{1-6}$alkyl group, a hydroxyC$_{2-6}$alkyl group, or a halogenoC$_{1-6}$alkyl group, R$^b$ and R$^c$ are identical or different, and each represents a C$_{1-6}$alkyl group, a C$_{1-6}$alkoxy group, a hydroxyC$_{2-6}$alkyl group, or a halogenoC$_{1-6}$alkyl group, and R$^4$ and R$^{4'}$ are identical or different, and each represents a hydrogen atom, or a C$_{1-6}$alkyl group.

It is preferred that in formula [III],

Z represents —O—,

R$^a$ represents a C$_{1-6}$alkyl group, or a halogenoC$_{1-6}$alkyl group,

R$^b$ and R$^c$ are identical or different, and each represents a C$_{1-6}$alkyl group, or a halogenoC$_{1-6}$alkyl group, and R$^4$ and R$^{4'}$ are identical or different, and each represents a C$_{1-6}$alkyl group.

It is preferred that in formula [III],

Z represents —O—,

R$^a$ represents a C$_{1-3}$alkyl group,

R$^b$ and R$^c$ are identical or different, and each represents a C$_{1-3}$alkyl group, and R⁴ and R⁴' are identical or different, and each represents a C$_{1-3}$alkyl group.

A further preferred the BBG derivative, a pharmaceutically acceptable salt thereof or a hydrate thereof is a BBG dye.

The C$_{1-10}$alkyl group means a straight-chain alkyl group having one to ten carbon atoms, a branched chain alkyl group having three to ten carbon atoms or a cyclic alkyl group having three to ten carbon atoms. Examples of the straight-chain alkyl group include a methyl group, an ethyl group, a propyl group, a butyl group, a pentyl group, a hexyl group, a heptyl group, an octyl group, a nonyl group and a decyl group. Examples of the branched chain alkyl group include an isopropyl group, an isobutyl group, a 1-methylpropyl group, a t-butyl group, a 1-methylbutyl group, a 2-methylbutyl group, a 3-methylbutyl group, a 1-ethylpropyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 5-methylhexyl group, a 3-ethylpentyl group, a 1-propylbutyl group, a 1,4-dimethylpentyl group, a 3,4-dimethylpentyl group, a 1,2,3-trimethylbutyl group, a 1-isopropylbutyl group, a 4,4-dimethylpentyl group, a 5-methylheptyl group, a 6-methylheptyl group, a 4-ethylhexyl group, a 2-propylpentyl group, a 2,5-dimethylhexyl group, a 4,5-dimethylhexyl group, a 2-ethyl-3-methylpentyl group, a 1,2,4-trimethylpentyl group, a 2-methyl-1-isopropylbutyl group, a 3-methyloctyl group, a 2,5-dimethylheptyl group, a 1-(1-methylpropyl)-2-methylbutyl group, a 1,4,5-trimethylhexyl group, a 1,2,3,4-tetramethylpentyl group, a 7-methyloctyl group, a 6-methylnonyl group, a 8-methylnonyl group, a 5-ethyl-2-methylheptyl group, a 2,3-dimethyl-1-(1-methylpropyl)butyl group, a cyclopropylmethyl group, a 2-(cyclopropyl)ethyl group, a 3,7-dimethyloctyl group, a 3-(cyclobutyl)pentyl group, a cyclopentylmethyl group and a cyclohexylmethyl group. Examples of the cyclic alkyl group include a cyclopropyl group, a cyclobutyl group, a cyclopentyl group, a cyclohexyl group, a cycloheptyl group and a cyclooctyl group. In the C$_{1-10}$alkyl group, a C$_{1-6}$alkyl group is preferred, and a C$_{1-3}$alkyl group is further preferred.

The C$_{2-10}$alkenyl group means a straight-chain alkenyl group having two to ten carbon atoms with at least one double bond, a branched chain alkenyl group having three to ten carbon atoms or a cyclic alkenyl group having five to ten carbon atoms, examples of which include a vinyl group, an allyl group, a 3-butenyl group, a 4-pentenyl group, a 5-hexenyl group, a 6-heptenyl group, a 7-octenyl group, a 8-nonenyl group, a 9-decenyl group, a 1-methyl-2-butenyl group, a 2-methyl-2-butenyl group, a 2-methyl-3-butenyl group, a 2-pentenyl group, a 2-methyl-2-hexenyl group and a 2-cyclopentenyl group. In the C$_{2-10}$alkenyl group, a C$_{2-6}$alkenyl group is preferred, and a C$_{2-3}$alkenyl group is further preferred.

The C$_{2-10}$alkynyl group means a straight-chain alkynyl group having two to ten carbon atoms with at least one triple bond or a branched chain alkynyl group having four to ten carbon atom, examples of which include a 2-propynyl group, a 3-butynyl group, a 4-pentynyl group, a 5-hexynyl group, a 6-heptynyl group, a 7-octynyl group, a 8-nonynyl group, a 9-decinyl group, a 3-pentynyl group and a 4-methyl-2-pentynyl group. In the C$_{2-10}$alkynyl group, a C$_{2-6}$ alkynyl group is preferred, and a C$_{2-3}$alkynyl group is further preferred.

The C$_{1-10}$alkyl group substituted by one or two aryl groups means, for example, a benzyl group, a diphenylmethyl group, a 2-phenyethyl group, a 2-phenylpropyl group, a 1-methyl-1-phenyethyl group, a 1-methyl-2-phenylpentyl group, a 2-nitrobenzyl group, a 3-nitrobenzyl group, a 4-nitrobenzyl group, a 2,4-dinitrobenzyl group, a 2,4,6-trinitrobenzyl group, a 2-phenylbenzyl group, a 3-phenylbenzyl group, a 4-phenylbenzyl group, a 2-hydroxybenzyl group, a 3-hydroxybenzyl group, a 4-hydroxybenzyl group, a 2-chlorobenzyl group, a 3-chlorobenzyl group, a 4-chlorobenzyl group, a 2-fluorobenzyl group, a 3-fluorobenzyl group, a 4-fluorobenzyl group, a 2-beromobenzyl group, a 3-beromobenzyl group, a 4-beromobenzyl group, a 2-iodobenzyl group, a 2-iodobenzyl group, a 2,3-dichlorobenzyl group, a 2,4-dichlorobenzyl group, a 2,5-dichlorobenzyl group, a 2,6-dichlorobenzyl group, a 3,4-dichlorobenzyl group, a 3,5-dichlorobenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-isopropylbenzyl group, a 3-isopropylbenzyl group, a 4-isopropylbenzyl group, a 2-methoxybenzyl group, a 3-methoxybenzyl group, a 4-methoxybenzyl group, a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, a 3,5-dimethoxybenzyl group, a 2-ethoxybenzyl group, a 3-ethoxybenzyl group, a 4-ethoxybenzyl group, a 2-isopropoxybenzyl group, a 3-isopropoxybenzyl group, a 4-isopropoxybenzyl group, a 2-methoxymethylbenzyl group, a 3-methoxymethylbenzyl group, a 4-methoxymethylbenzyl group, a 2-isopropyxymethylbenzyl group, a 3-isopropyxymethylbenzyl group, a 4-isopropyxymethylbenzyl group, a 2-trifluoromethyl group, a 3-trifluoromethyl group, a 4-trifluoromethyl group, a 2-hydroxycarbonylbenzyl group, a 3-hydroxycarbonylbenzyl group, a 4-hydroxycarbonylbenzyl group, a 2-aminobenzyl group, a 3-aminobenzyl group, a 4-aminobenzyl group, a 2-aminomethylbenzyl group, a 3-aminomethylbenzyl group, a 4-aminomethylbenzyl group, a 2-cyanobenzyl group, a 3-cyanobenzyl group, a 4-cyanobenzyl group, a 2-hydroxymethylbenzyl group, a 3-hydroxymethylbenzyl group, a 4-hydroxymethylbenzyl group, a 2-phenoxybenzyl group, a 3-phenoxybenzyl group and a 4-phenoxybenzyl group. As the C$_{1-10}$alkyl group of the C$_{1-10}$alkyl group of substituted by one or two aryl groups, a C$_{1-6}$alkyl group is preferred, and a C$_{1-3}$alkyl group is further preferred.

The aryl group means a phenyl group, a substituted phenyl group or a polycyclic aromatic group such as a 1-naphthyl group or a 2-naphthyl group.

The hydroxyC$_{2-10}$alkyl group means a C$_{2-10}$alkyl group substituted by at least one hydroxyl group, examples of which include a 2-hydroxyethyl group, a 3-hydroxypropyl group, a 4-hydroxybutyl group, a 5-hydroxypentyl group, a 6-hydroxyhexyl group, a 7-hydroxyheptyl group, a 8-hydroxyoctyl group, a 9-hydroxynonyl group, a 10-hydroxydecyl group, a 2-hydroxypropyl group, a 2,3-dihydroxypropyl group and a 2-hydroxy-3-methylbutyl group. In the hydroxyC$_{2-10}$alkyl group, a hydroxyC$_{2-6}$alkyl group is preferred, and a hydroxyC$_{2-3}$alkyl group is further preferred.

The halogenoC$_{1-10}$alkyl group means a C$_{1-10}$alkyl group substituted by at least one fluorine atom, chlorine atom, bromine atom or iodine atom, examples of which include a 2-chloroethyl group, a 2-bromoethyl group, a 2-iodoethyl group, a 3-chloropropyl group, a 3-bromopropyl group, a 3-iodopropyl group, a 4-chlorobutyl group, a 4-bromobutyl group, a 4-iodobutyl group, a 5-chloropentyl group, a 6-chlorohexyl group, a 7-chloroheptyl group, a 8-chlorooctyl group, a 9-chlorononyl group, a 10-chlorodecyl group, a 2-chloropropyl group, a 2-chlorobutyl group, a 2,4-dichlorobutyl group and a 2-chloro-3-methylbutyl group. In the halogenoC$_{1-10}$alkyl group, a halogenoC$_{1-6}$alkyl group is preferred, and a halogenoC$_{1-10}$alkyl group is further preferred.

The C$_{1-10}$alkoxyC$_{1-10}$alkyl group means a alkyl group having one to ten carbons which is substituted by a straight-chain alkoxy group having one to ten carbons, a branched chain alkoxy group having three to ten carbon atoms or a cyclic alkoxy group having three to ten carbon atoms, examples of which include a 2-methoxyethyl group, a 2-ethoxyethyl group, a 2-propoxyethyl group, a 2-isopropoxyethyl group, a 2-butoxyethyl group, a 2-isobutoxyethyl group, a 2-t-butoxyethyl group, a 2-pentyloxyethyl group, a 2-hexenyloxyethyl group, a 3-ethoxypropyl group, a 4-ethoxybutyl group, a 4-ethoxy-3-methoxybutyl group and a 4-ethoxy-3-methylpentyl group. In the C$_{1-10}$alkoxyC$_{1-10}$alkyl group, a C$_{1-6}$alkoxyC$_{1-6}$alkyl group is preferred, and a C$_{1-3}$alkoxyC$_{1-3}$alkyl group is further preferred.

The halogenoC$_{1-10}$alkoxy group means a C$_{1-10}$alkoxy group substituted by at least one fluorine atom, chlorine atom, bromine atom or iodine atom. In the halogenoC$_{1-10}$alkoxy group, a halogenoC$_{1-6}$alkoxy group is preferred, and a halogenoC$_{1-3}$alkoxy group is further preferred.

The preferred stereostructure of the BBG derivative of the present invention is optically active bodies having the absolute structure, but the BBG derivative of the present invention may be present as enantiomers or enantiomer mixtures such as racemic bodies. Therefore, the BBG derivative of the present invention includes all of the optically active bodies, the enantiomer mixtures such as racemic bodies and the diastereomer mixtures of the BBG derivative represented by the above formula [I].

Examples of the pharmaceutically acceptable salt includes salts formed with inorganic bases, ammonia, organic bases, inorganic acids, organic acids, basic amino acids, halogen ions or the like, and inner molecular salts. Examples of the inorganic base include alkaline metal (e.g., Na, K) and alkaline earth metal (e.g., Ca, Mg). Examples of the organic base include trimethylamine, triethylamine, choline, procaine, ethanolamine and the like. Examples of the inorganic acid include hydrochloric acid, hydrobromic acid, sulfuric acid, nitric acid, and phosphoric acid and the like. Examples of the organic acid include p-toluene sulfonic acid, methanesulfonic acid, formic acid, trifluoroacetic acid and maleic acid and the like. Examples of the basic amino acid include lysine, arginine, ornithine, histidine and the like. The compound may be a pharmaceutically acceptable hydrate.

The BBG derivative of the present invention, a pharmaceutically acceptable salt thereof or a hydrate thereof, especially BBG, may be purchased and manufactured by using common knowledge of organic chemistry. Further, they may be manufactured by the method disclosed in the specification of the U.S. Pat. No. 6,057,160 and the document is hereby incorporated by reference.

One embodiment of the present invention will be described using practical examples and drawings, as follows.

First, all dyes, including dyes not currently being used for organisms were utilized, and then screened for candidate dyes. The dyes screened are Evans blue, Acid blue 9, Fast green, Brilliant Blue FCF, Indigo-carmine, methyl blue, methylene blue, Brilliant Blue G (BBG). The screening conditions focused in particular on staining-affinity and safety. Among some of the leading candidates, those that showed superiority in safety but inability to dye the target object, or in the reverse, those that showed good staining but virulence to the retina, were removed from candidacy. Safety assessments of the narrowed down candidates were conducted using rats, and in accordance with better staining-affinity and safety, BBG was made the final candidate. The following describes in detail the reasons why BBG became the final candidate for the present invention.

First, BBG's staining qualities, when compared with ICG's, were very similar, and it can stain a target object at very low concentrations (1/10-1/20). Even upon examination of very high concentration solutions remaining behind at the intraocular, no opinion could be proven regarding clear toxicity to the eye. Additionally, because BBG (unlike ICG) is not a fluorescent dye, phototoxicity to the retina that is believed to occur due to intraocular illumination from high illuminance can be thought to be almost non-existent. Furthermore, persistence of the dye on the tissue surface after cleansing was, compared with ICG, very low. Then again, because BBG is a cool color type dye, with the intraocular tissues being a warm color type, the contrast of the dye can be emphasized.

Next, various experiments were conducted to assess the optimal conditions of a staining composition containing BBG for dyeing an ophthalmic membrane. Furthermore, BBG until now has not been used clinically, particularly with regard to humans. However, via such optimal conditions of the present invention, one can provide a composition which is both safe and has high staining-affinity for clinical usages.

Therefore, according to the first main aspect of the present invention, a staining composition is provided which has BBG derivative as a principal component, for staining an ophthalmic membrane at the time of removal of the ophthalmic membrane.

According to one preferred embodiment of the present invention, said staining composition can be used as a surgical adjuvant in opthalmological surgeries with regard to diseases of the eye such as, for example, vitreo-retinal disease such as Macular hole, retinal detachment due to hymyopic macular hole, epiretinal membrane, proliferative diabetic retinopathy, diabetic macular edema, and proliferative vitreoretinopathy, specific cataracts such as hypermature cataract, and congenital cataract, and so on, as well as split-thickness corneal transplantation and so on. According to the staining composition of the present invention, it becomes possible to more clearly verify difficult-to-see ophthalmic membranes, and improve safety during surgical operations.

In a further preferred embodiment of the present invention, said staining composition can be used for staining an ophthalmic membrane and more preferably, for staining the internal limiting membrane and/or the anterior capsule.

Then again, according to one embodiment of the present invention, the staining composition of the present invention can be combined with a pharmaceutically acceptable carrier. It can be prepared in the form of a set with a dissolving solution and drug powders, or as a solution filled up in a syringe receptacle, and in a gel-state solution when combined with a hyaluronic acid. Most preferably, it is prepared in the form of a solution, but it need not be limited to that.

In one embodiment of the present invention, said staining composition is prepared as a pharmaceutically acceptable solution, although it need not necessarily be limited to that. This results from the qualities of BBG where it can be directly and easily dissolved in an intraocular cleansing solution, and can be sterilized with the syringe filter.

Furthermore, according to one embodiment of the present invention, said staining composition is prepared as a solution where it is dissolved in an intraocular irrigating solution, a balanced salt solution (BSS), a physiological saline solution, or most preferably, OPEGUARD-MA (Senjyu Pharmaceutical Co., Ltd., Osaka, Japan) which is an intraocular irrigating solution (intraocular cleansing solution). However, it need not be limited to that form.

In one preferred embodiment of the present invention, the staining composition contains BBG at a concentration of 0.1-10 mg/ml, preferably a concentration of 0.1-1.0 mg/ml, and most preferably, a concentration of 0.1-0.25 mg/ml. In one practical example of the present invention, in said staining composition, the concentration of BBG required to stain the ILM of primates, is about 1/10 in comparison with ICG. Additionally, for staining of the anterior capsule, the BBG within said staining composition can provide satisfactory staining with a low concentration of 0.25 mg/ml, as compared to ICG's requiring 5 mg/ml and TB's requiring 1 mg/ml. In other words, according to this embodiment, a staining composition can be provided which has high staining-affinity at low concentrations and small quantities.

Furthermore, it is preferable according to one embodiment of the present invention for the staining composition to have an osmotic pressure in the environs of 298 mOsm. According to this embodiment, the staining composition of the present invention has an osmotic pressure equal to a physiological saline solution. It was previously reported that defects in the retinal pigment epithelium with ICG, may possibly originate from the hypoosmolality of its solution. With regard to this, the staining composition of one embodiment of the present invention has superior effects, in that defects caused by differences in osmotic pressure at the retinal pigment epithelium—which are tissue disorders relating to cell expansions or dehydration (such as cell omission or cell death)—do not occur.

In one preferred embodiment of the present invention, it is desirable that the staining composition of the present invention displays a neutral pH, that is, a pH in the vicinity of pH=7.4.

According to the second main aspect of the present invention, a method for staining and removing an ophthalmic membrane is provided having the steps of preparing a staining composition having BBG derivative as a principal component; staining the ophthalmic membrane using a predetermined concentration of said staining composition; and removing the stained ophthalmic membrane.

For one embodiment of the present invention, said method for staining the ophthalmic membrane can use a method easily understood by one skilled in the art, for example, injection, infusion, irrigation, confirmation and peeling. In one practical example of the present invention, it is preferable that said method for staining an ophthalmic membrane involves the injection of said staining composition. With this practical example, an additional step such as fluid-gas exchange, which is required when applying TB to an ophthalmic membrane, is not necessary. As an example, it is possible to simply stain at the time of use during ophthalmic surgery.

According to the third main aspect of the present invention, a use of BBG derivative in the manufacture of a staining composition for the treatment of ophthalmic diseases is provided.

Additionally, according to the fourth main aspect of the present invention, a use of BBG derivative as a surgical adjuvant for ophthalmic surgeries is provided.

Furthermore, in one embodiment of the present invention, said staining composition and/or a staining method utilizing it, can be suitably employed as a part of ophthalmic surgeries. According to a preferred embodiment of the present invention, said opthalmological surgeries are surgeries for treating macular hole, retinal detachment due to hymyopic macular hole, epiretinal membrane, proliferative diabetic retinopathy, diabetic macular edema, and proliferative vitreoretinopathy, specific cataracts such as hypermature cataract, and congenital cataract, and split-thickness corneal transplantation, and so on, and most preferably, vitreo-retinal diseases (in particular macular hole or epiretinal membranes (ERMS)) and cataracts.

Furthermore, with one preferred embodiment of the present invention, said ophthalmic surgeries are put into effect on the eyes of mammals and, more preferably, on the eyes of humans.

The following examples are provided to describe the invention in greater detail. They are intended to illustrate, not to limit, the present invention.

Example 1

Screening Various Dyes as a Candidate Focusing on their Safety and Ability to Stain Membranes In order to provide a staining composition for achieving such aims, all dyes, including dyes currently not being utilized for organisms were used, and they were then screened for candidate dyes. The dyes screened are Evans blue, Acid blue 9, Fast green, Brilliant Blue FCF, Indigo-carmine, methyl blue, methylene blue, Brilliant Blue G (BBG). Additionally, as the screening conditions, safety and staining-affinity were especially noted.

Among some of the leading candidates, those that showed superiority in safety but inability to dye the target object, or in the reverse, those that showed good staining but virulence to the retina, were removed from candidacy.

Safety assessments were then conducted, using rats, of the narrowed down candidate dyes. Based on higher staining-affinity and safety, BBG became the final candidate.

Next, in order to examine the optimal conditions of a staining composition containing BBG for staining an ophthalmic membrane, various experiments were performed. In that way, the staining composition of the present invention was achieved.

Example 2

2. Effects of the Intravitreous BBG on the Retina

All procedures conformed to the Association for Research in Vision and Opthalmology (ARVO) statement for the Use of Animals in Ophthalmic and Vision Research and the guidelines for animal care at Kyushu University, Fukuoka, Japan.

2.1 Characterization of the BBG Solution

BBG is also known as Acid Blue 90 and Coomassie Brilliant Blue G. Aside from our previous publication, there are no reports investigating the toxicity BBG for ophthalmic use. Table 1 shows the osmolarity and pH of the BBG solution at different concentrations. The osmolarity and pH of BBG was found to be similar to those of intraocular irrigating solutions.

TABLE 1

| solution | Osmolarity (mOsm/KgH$_2$0) | pH |
| --- | --- | --- |
| control | 298 | 7.33 |
| BBG 10 mg/ml | 310 | 7.41 |
| BBG 1.0 mg/ml | 300 | 7.42 |
| BBG 0.1 mg/ml | 298 | 7.41 |
| BBG 0.01 mg/ml | 298 | 7.41 |
| saline | 285 | 7.4 |

TABLE 1-continued

| solution | Osmolarity (mOsm/KgH$_2$0) | pH |
|---|---|---|
| BSS plus (Registered trademark) | 305 | 7.1 |

Control shows OPEGUARD ® - MA.

2.2. Surgical Procedure for Intravitreal BBG in Rat Eyes

Brown Norway rats (n=78 males, 8 weeks old, Kyudo, Fukuoka, Japan) were anesthetized with an intraperitoneal injection of ketamine hydrochloride at a dose of 75 mg/kg body weight. One eye from each animal (total of n=6 per dose group) was vitrectomized using 0.05 ml of pure SF$_6$ gas as described previously. Following the gas injection, 0.05 ml of BBG solution was injected into the vitreous cavity of each vitrectomized eye using a microscope for enhanced magnification during surgery. The BBG solution (Brilliant Blue G, Coomassie (Registered trademark) brilliant blue G 250; Signa-Aldrich, St. Louis, USA) was prepared at concentrations of 0.01, 0.1, 1.0, and 10 mg/ml using dilution in intraocular irrigating solution (OPEGUARD (Registered trademark)-MA, Senjyu Pharmaceutical Co. Ltd., Osaka, Japan), and sterilized through a 0.22 μm syringe filter. The mean osmolality was determined using an osmotic pressure meter (OSMO STATION, Arkray, Kyoto, Japan) and the pH of each solution was determined for all concentrations prepared (Table 1). The final concentration was determined according to the ICG solution used in vitrectomies for humans (2.5-5.0 mg/ml), in order to provide the rats with a safe dose of BBG that would also produce good staining. Twenty-four sham-operated eyes (injected with SF$_6$ followed by 0.05 ml of intraocular irrigating solution) were used as controls.

2.3. Light Microscopy

The eyes were enucleated and fixed in 10% paraformaldehyde on day 14 (n=30; 6 per dose and control group) and at 2 months (n=30; 6 per dose and control group) post-operatively. Whole eyes were cut approximately along the vertical meridian. Paraffin-embedded sections were stained with hematoxyline-eosin (HE) and each section was examined using light microscopy.

After intravitreal injection of BBG, no toxic effects of BBG such as corneal edema, severe retinal edema, or endophthalmitis were observed by surgical microscopy over a period of 2 months. The eyes were enucleated on day 14 and 2 months after the operation. The normal structure of the retina was preserved in the eyes injected with the highest doses of BBG (10 mg/ml) when observed on both day 14 and at 2 months. In addition, no infiltration of inflammatory cells was observed. (FIG. 1, day 14) The normal structure of retina was also retained in the groups injected with lower doses of BBG and no sign of cellular degeneration was observed in the sections on day 14 or at 2 months.

2.4. Transmission Electron Microscopy (TEM)

The eyes were enucleated on day 14 and at 2 months post-operation and fixed in 1% glutaraldehyde and 1% paraformaldehyde in PBS. The specimens were postfixed in veronal acetate buffer osmium tetroxide (2%), dehydrated in ethanol and water, and embedded in Epon. Ultrathin sections were cut from blocks and mounted on copper grids. The specimens were observed with a JEM 100CX electron microscope (JEOL, Tokyo).

Figure 2:
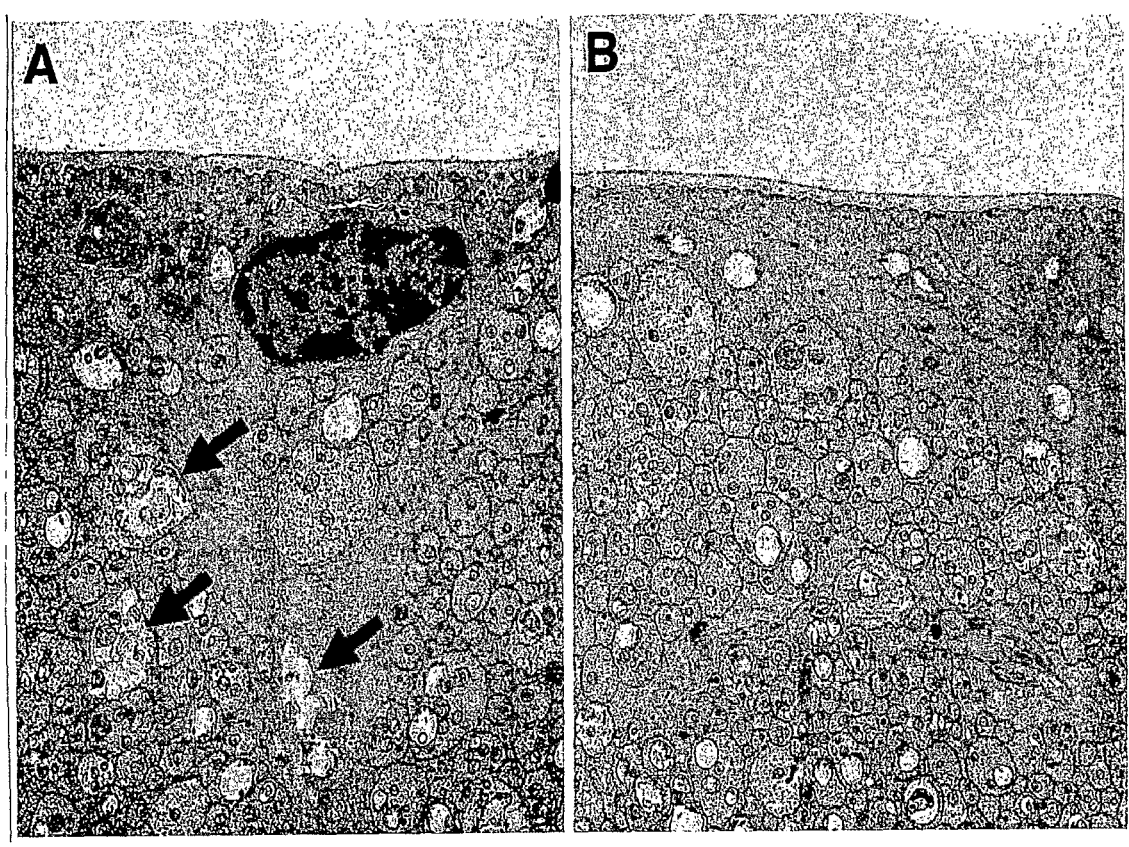
FIG. 2 shows transmission electron microscopic photography of the rat eyes injected with intravitreal BBG (10 mg/ml and 1 mg/ml, 0.05 ml/eye) visualized at 14 days. (Original Magnification ×2000)

Some specimens injected with the highest dose of BBG (10 mg/ml) showed vacuolization in the ganglion cells and Müller cell processes of nerve fibers on both day 14 (FIG. 2A, day 14) and at 2 months. Although the same changes were also found in the group injected with 1 mg/ml BBG, the grade of vacuolization was less than in the 10 mg/ml group (FIG. 2B). Vacuolization was not observed in the groups receiving lower doses or in the controls. Among all groups, no remarkable changes were observed in the retina including the inner nuclear, outer nuclear, and retinal pigment epithelial cell layers.

2.5. TdT-dUTP Terminal Nick-End Labeling (TUNEL)

Apoptotic cell death was detected using TdT-dUTP Terminal Nick-End Labeling (TUNEL) as described previously. A cryostat was used to produce 4-μm sections from samples fixed in 4% paraformaldehyde and embedded in paraffin. TUNEL staining was performed with the ApopTag® Fluorescein Direct in situ Apoptosis Detection Kit (Intergen Company, New York, USA) according to the manufacturer's protocol. The sections were co-stained with propidium iodide (Molecular Probes, Eugene, Oreg., USA), thus allowing the observation of the cell nuclei by a fluorescence microscope (Olympus, Tokyo). Ten sections from each eye specimen were selected at random and observed using the microscope.

Figure 3:
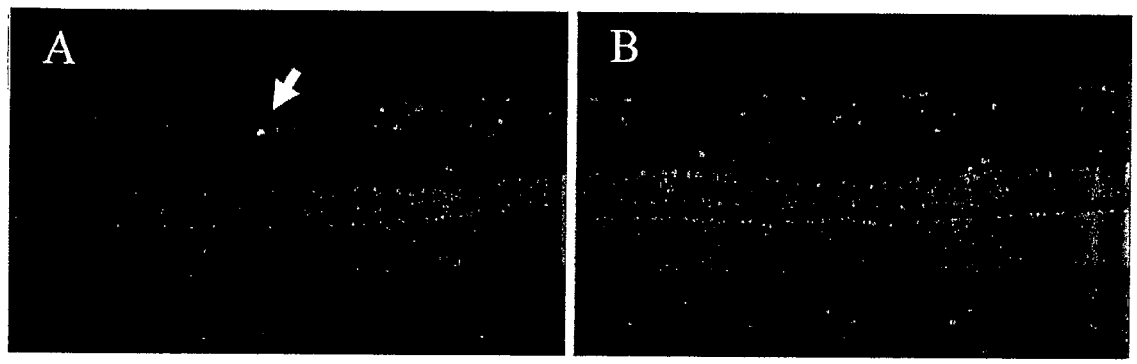
FIG. 3 shows a photography showing apoptotic cell death detected by TUNEL. (Original magnification ×400)

In the group administered the highest doses of BBG (10 mg/ml) group, one case of apoptotic cell death was observed from among ten sections. However, the apoptotic cell ratio was not significantly different to that observed in control sections (FIG. 3, day 14). In groups injected with lower doses of BBG, no TUNEL staining was observed in the retina on day 14. Furthermore, retinal cells in all BBG dose groups had not undergone apoptotic cell death after 2 months.

2.6. Electroretinography

Following a gas injection, 0.05 ml of BBG solution (1 mg/ml and 10 mg/ml) or intraocular irrigating solution was injected into the vitreous cavity. There were six rats in each dose group and six controls. The absence of cataracts was confirmed in all rats before measurements were taken. At time points of fourteen days, and again at two months later, the rats were kept in a dark room for one night, with only dim red illumination, and anesthetized with an intraperitoneal injection of 15 μl/g body weight of a saline solution containing ketamine (1 mg/ml), xylazine (0.4 mg/ml), and urethane (40 mg/ml). Electroretinography (ERG) was then performed as previously described. The pupils were dilated with 2.5% phenylephrine HCl and 1% tropicamide drops, and showed maximal dilatation before ERG recording. The cornea was anesthetized with 1% proparacaine HCl drops and the rats were then placed on a heating pad throughout the experiment. A wire electrode, coated with 1% methylcellulose, was placed over the cornea to record the ERGs. A similar wire electrode placed in the mouth served as a reference electrode while a needle electrode inserted into the tail was grounded. The responses were differentially amplified (0.8 to 1,200 Hz), averaged, and stored using a computer. White (xenon) strobe flashes were presented in a Ganzfeld stimulator (VPA-10; Cadwell, Kennewick, Wash., USA) against an achromatic adapting field. Dark-adapted (rod-mediated) ERGs were recorded first to check the response stability at both intensities. Each rat was then adapted to dark background luminance for 20 minutes, a period sufficient to achieve a stable level of response. Thereafter, dark-adapted a (rod-mediated) and dark-adapted b (bipolar and Müller-mediated) ERGs were elicited at a flash luminance of 1.30 log cd sec/m$^2$. The responses to five successive flashes at an interstimulus interval of 1 min were then averaged to determine the dark-adapted responses. The rats were then exposed to a white light-adapting field (1.50 log cd/m$^2$) for at least 25 minutes and then light-adapted b (cone-mediated) ERGs were elicited at a flash luminance of 1.30 log cd sec/m$^2$ (rod desensitized condition in rats). The responses to 50 successive flashes made at 2 Hz were averaged. The results of the amplitude of ERGs were evaluated using the Student's t test and a p value of <0.05 was considered statistically significant.

Figure 4:
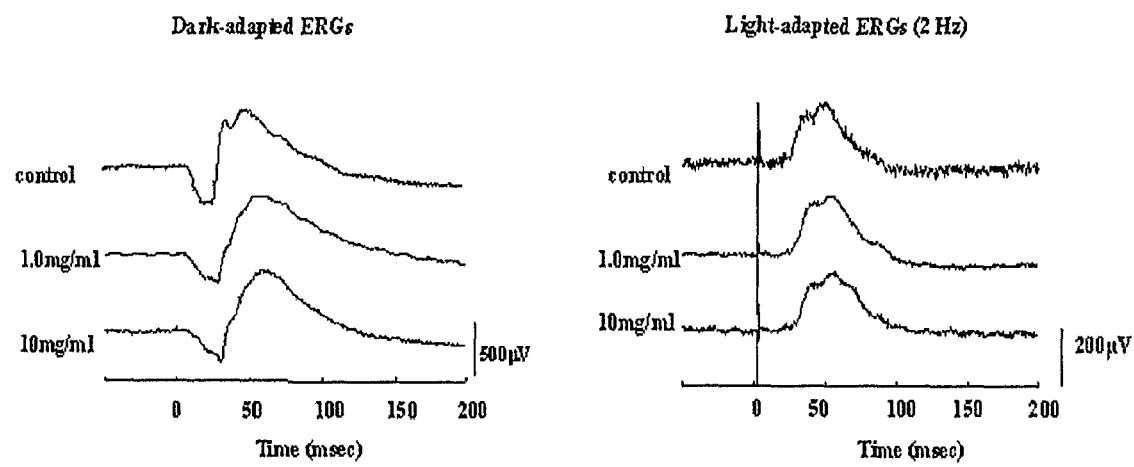
FIG. 4 shows graphs showing Wave forms and maximal amplitude of ERGs in rat eyes.
Figure 4:
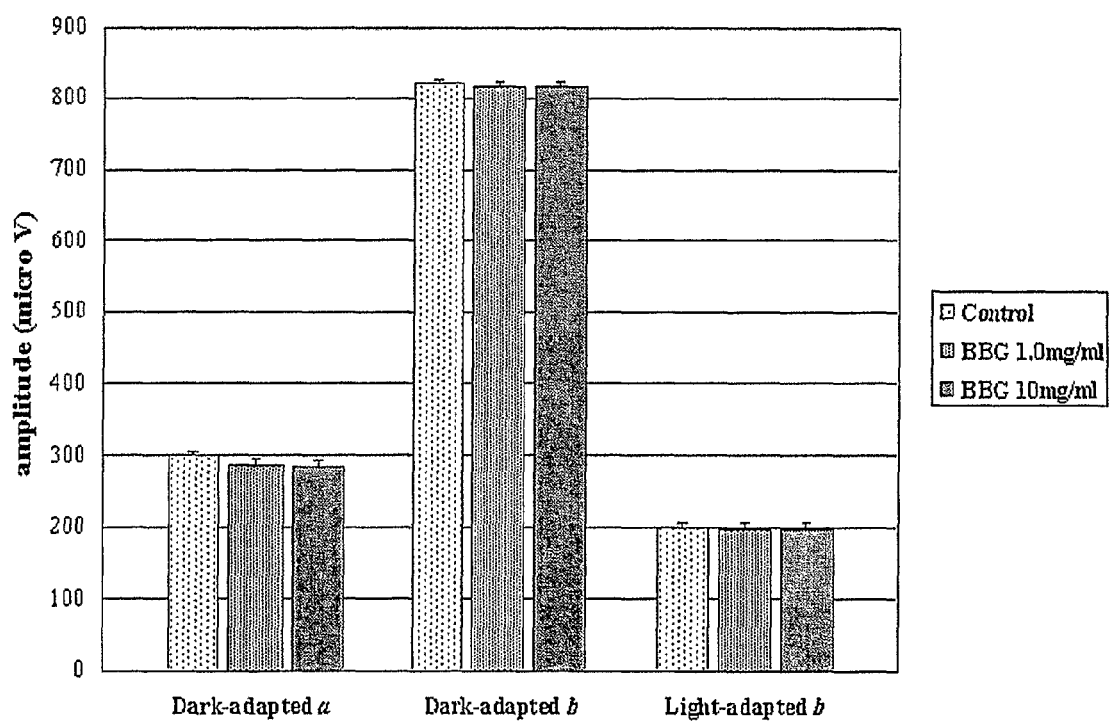

FIG. 4A represents the dark- and light-adapted ERG wave forms of the responses of the control and high does groups on day 14. The amplitudes of dark-adapted responses obtained at the beginning of the experiments showed a low variability between groups. Although a slight reduction in the mean maximal amplitude of the dark-adapted a waves (FIG. 4B, day 14) on day 14 was observed in a dose dependent manner in the high dose groups, there was no significant difference in the maximal wave amplitude compared with the controls (10 mg/ml: p=0.054 and 1.0 mg/ml: p=0.063; t test). Also, dark-adapted b waves (10 mg/ml: p=0.553 and 1.0 mg/ml: p=0.508; t test) and light-adapted b wave ERGs (10 mg/ml: p=0.451 and 1.0 mg/ml: p=0.550; t test) demonstrated no remarkable reduction, with no statistical significant difference between the amplitudes (FIG. 4B, day 14). After 2 months the ERGs in the same dose groups (1.0 mg/ml and 10 mg/ml) were recorded and the reduction of the amplitude of the dark-adapted a waves was found to recover in a similar manner to that in the control group.

2.7. ILM Staining by BBG in Primate Eyes

Since ILM peeling is impossible in rat eyes, the inventors examined the ability of BBG to stain the ILM in primate eyes. Two eyes from two cynomolgus monkeys at 3 years of age were used in this study. The animals were restrained in a squeeze cage and injected intramuscularly in the thigh with 20 mg/kg of ketamine hydrochloride (Sankyo Yell Pharmaceutical Products Co. Ltd., Japan) for general anesthesia. The monkeys were subsequently transported to an operating room. Surgery consisted of a standard three port pars plana vitrectomy with induction of a posterior vitreous detachment by suction with a vitrectomy cutter using triamcinolone acetonide injection for vitreous visualization.

Ten milligrams of BBG were dissolved in 20 ml of intraocular irrigating solution and sterilized with a syringe filter. The final concentration of BBG was 0.5 mg/ml. The prepared BBG solution (0.5 ml) was then injected gently into the vitreous cavity and washed out immediately with balanced salt solution (BSS Plus (Registered trademark), Santen, Osaka, Japan). Removal of the ILM was performed using ILM forceps. The instruments were then removed and the sclerotomy ports were closed using 7-0 polygalatin sutures. Postoperative examinations included slitlamp microscopy and opthalmoscopy on days 1, 3 and 14. Fluorescein angiography was performed, on day 14.

Figure 5:
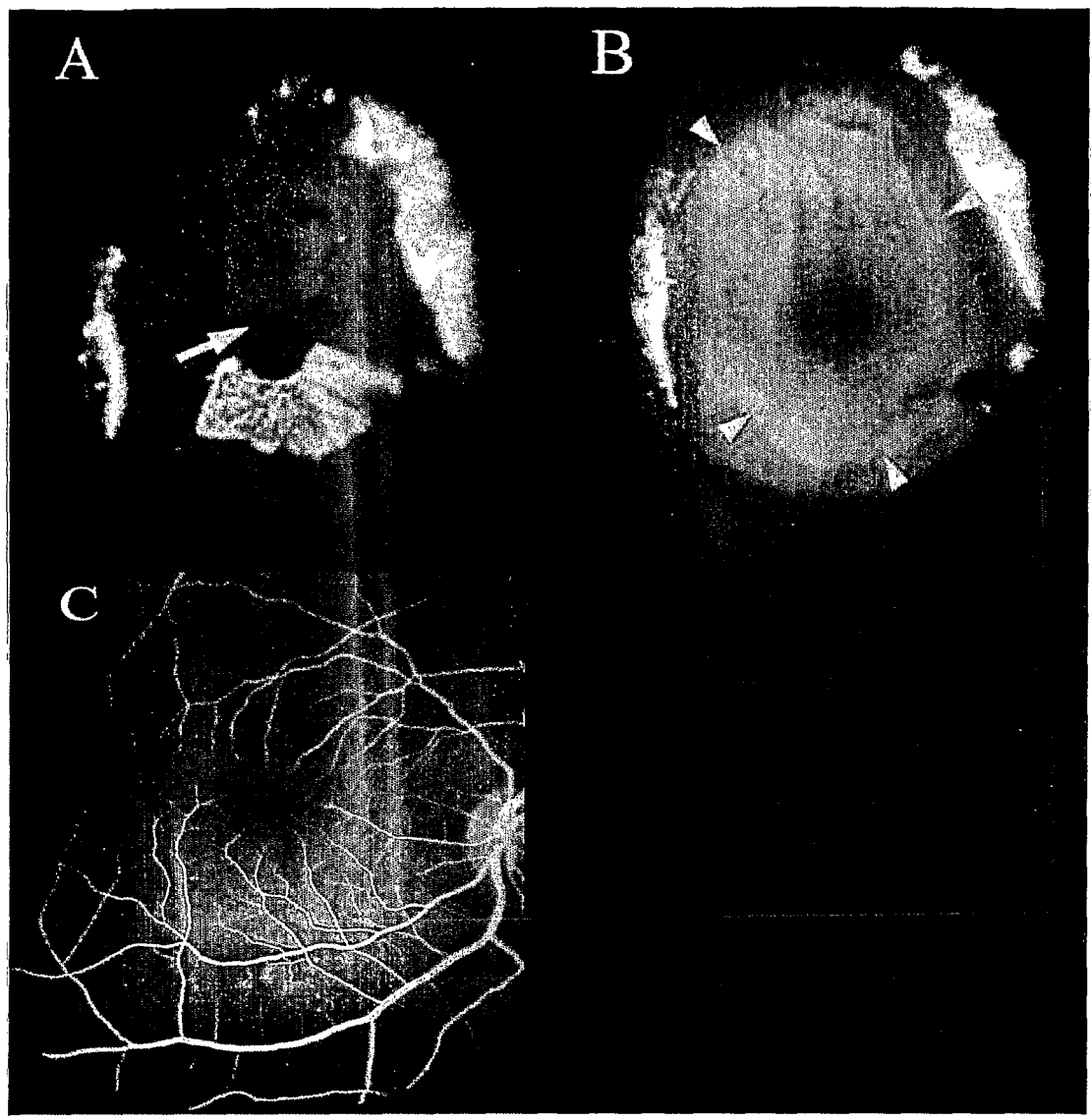
FIG. 5 shows photographs showing ILM staining by BBG in primate eyes

After irrigation of the vitreous cavity, the ILM was stained a light blue color. The edge and flap of the ILM were clearly visible during the peeling of the ILM (FIG. 5A). The circular area underlying the ILM was clearly visible following the peeling of the ILM (FIG. 5B).

Postoperatively, toxic effects of BBG, such as a corneal edema, severe retinal edema and endophthalmitis, were not observed during slitlamp microscopy and opthalmoscopy examinations at day 14. Fluorescein angiography also revealed that there was no apparent retinal damage by BBG on day 14 (FIG. 5C). Further opthalmoscopic examinations showed no further changes in the retina during the six-month follow-up period.

Example 3

3. Interventional Clinical Case Series of BBG as a Potential Staining Solution for Membrane Peeling Indocyanine green (ICG) and Trypan Blue (TB) staining have greatly facilitated ILM peeling in various vitreo-retinal diseases. However, numerous reports have recently emerged regarding retinal damage caused by ICG and TB both in experimental and clinical use.

From the preclinical study, BBG was selected as a candidate dye for ILM staining. This is apparently the first clinical investigation of BBG in human eyes. This is the first known clinical investigation of BBG in human eyes.

3.1. The Use of BBG in ILM Staining and the Effects and Safety in Human Eyes (the First Attempt)

Sixteen eyes of 16 patients with a macular hole (MH) and epiretinal membranes (ERMS) were recruited from the outpatient unit of Kyushu University Hospital (Fukuoka, Japan) between August and September 2004. Patients with ocular diseases such as glaucoma, uveitis, and corneal disorder were excluded. Characterization of the patients is shown in Table 1. This study was carried out with the approval from the appropriate institutional Ethics Committee and was performed in accordance with the ethical standards laid down in the 1989 Declaration of Helsinki. The possible advantages and risks of the present treatment were explained to the patients before surgery and informed consent was obtained from all patients. Surgery consisted of a three port pars plana vitrectomy with induction of a posterior vitreous detachment by suction with a vitrectony cutter using triamcinorone. Twenty milligrams of BBG (Brilliant blue G 250; Signa-Aldrich, St. Louis, USA) were dissolved in 10 ml of intraocular irrigating solution (OPEGUARD (Registered trademark)-MA, Senjyu Pharmaceutical Co., Ltd., Osaka, Japan) and sterilized with a syringe filter (Minisart (Registered trademark) Sartorius AG, Goettingen, Germany). The final concentration of BBG was 0.25 mg/ml. The prepared 0.5 ml of BBG solution (289 mOsm, pH=7.44) was then injected gently into the vitreous cavity and washed out immediately with balanced salt solution (BSS Plus (Registered trademark), Santen, Osaka, Japan). The ILM was stained a light blue color. Removal of the ILM was performed using ILM forceps (D.O.R.C.; Dutch Ophthalmic Research Center International b.v., Netherlands). However, staining of the ERMS could not be confirmed at this concentration.

Postoperative examinations included slitlamp microscopy, opthalmoscopy, best corrected visual acuity (BCVA) and intraocular pressure. The visual field was evaluated with Humphrey Field Analyzer II (Humphrey Systems, Dublin, Calif., USA) after 2 months.

The surgical procedure was completed successfully. Visual acuity recovered in all cases. None of the patients had an elevation of intraocular pressure. Apparent reduction of intensity and defect on visual field were not observed. No other adverse effects due to BBG were observed within the observation period. (Table 2)

TABLE 2

| case | disease | Age | Sex | Preop. BCVA | Postop. BCVA | ILM Peeling | Preop. Lens status | Follow Up (months) | Postop. Retinal status | Postop. IOP elevation | Postop. Defect Of VF | Postop. Lens status | complications |
|---|---|---|---|---|---|---|---|---|---|---|---|---|---|
| 1 | MH stage 3 | 58 | F | 20/63 | 20/20 | + | Phakic | 4 | MH closed | — | — | IOL | none |
| 2 | MH stage 4 | 77 | M | 20/200 | 20/63 | + | Phakic | 3 | MH closed | — | — | IOL | none |
| 3 | MH stage 3 | 57 | F | 20/50 | 20/50 | + | Phalic | 2 | MH closed | — | — | IOL | none |
| 4 | MH stage 2 | 62 | F | 20/100 | 20/25 | + | Phakic | 2 | MH closed | — | — | IOL | none |
| 5 | MH stage 3 | 68 | M | 20/100 | 20/50 | + | Phakic | 2 | MH closed | — | — | IOL | Peripheral Retibnal breake |
| 6 | MH stage 4 | 79 | M | 20/80 | 20/63 | + | IOL | 2 | MH closed | — | — | IOL | Peripheral Retibnal breake |
| 7 | MH stage 3 | 78 | M | 20/125 | 20/25 | + | Phakic | 2 | MH closed | — | — | IOL | none |
| 8 | MH stage 3 | 63 | F | 20/50 | 20/32 | + | Phakic | 2 | MH closed | — | — | IOL | none |
| 9 | MH stage 2 | 64 | F | 20/63 | 20/32 | + | Phakic | 2 | MH closed | — | — | IOL | none |
| 10 | ERM (secondary) | 33 | M | 20/63 | 20/32 | + | IOL | 4 | fold (−) | — | — | IOL | none |
| 11 | EMR (primary) | 85 | M | 20/40 | 20/32 | + | Phakic | 4 | Macular Cyst (+) | — | — | IOL | none |
| 12 | EMR (primary) | 72 | F | 20/63 | 20/40 | + | Phakic | 3 | fold (−) | — | — | IOL | none |
| 13 | EMR (primary) | 85 | M | 20/63 | 20/40 | + | Phakic | 3 | fold (−) | — | — | IOL | Vitreous bleesing |
| 14 | EMR (primary) | 66 | F | 20/40 | 20/12.5 | + | Phakic | 2 | fold (−) | — | — | IOL | none |
| 15 | EMR (primary) | 72 | M | 20/40 | 20/16 | + | Phakic | 2 | fold (−) | — | — | IOL | none |
| 16 | EMR (primary) | 63 | F | 20/63 | 20/40 | + | Phakic | 2 | Fold (−) | — | — | IOL | none |

Abbreviations of Table 2
MH: Macular hole,
ERM: Epiretinal membrane,
BCVA: Best-corrected visual acuity
preop.: Preoperation,
postop.: Postoperation,
IOL: Intraocular lens,
IOP: Intra ocular pressure,
VF: Visual field 3.2. The Use of BBG in ILM Staining and the Effects and Safety in Human Eyes (the Second Attempt)

The inventors have continued to investigate the clinical case, and obtained results as follows.

Twenty eyes from 20 consecutive patients presenting with macular hole (MH: ten eyes from 10 patients; 5 men and 5 women) or with epiretinal membrane (ERM: ten eyes from 10 patients, 5 men and 5 women) underwent vitrectomy with removal of the membranes using BBG staining solution between August and November 2004. Patients with ocular diseases such as glaucoma, diabetic retinopathy, uveitis, and corneal disorder were excluded. The mean±SD age of the patients was 67±11.9 years with a range of 33 to 85 years. The mean follow up period was 7.3±1.0 months. Patient details are tabulated in Table 3 and 4. Pre- and postoperative ophthalmic examinations included slitlamp microscopy, opthalmoscopy, best corrected visual acuity (BCVA) and intraocular pressure (IOP). The closure of the MH and measurement of foveal thickness (ERM cases) was determined by optical coherence tomography (OCT3: Humphrey Instruments, San Leandro, Calif., USA). The mean foveal thickness was calculated from a total of 4 scans.

Excised specimens from 4 eyes (2 eyes from MH patients and 2 eyes from ERM patients) were submitted for transmission electron microscopy to verify the presence of the ILM. The specimens were postfixed in veronal acetate buffer osmium tetroxide (2%), dehydrated in ethanol and water, and embedded in Epon. Ultrathin sections were cut from blocks and mounted on copper grids. The specimens were observed with a JEM 100CX electron microscope (JEOL, Tokyo).

This study was carried out with approval from the Institutional Review Board and performed in accordance with the ethical standards of the 1989 Declaration of Helsinki. The possible advantages and risks of the present treatment were explained to all patients before surgery and written informed consent obtained.

Figure 6:
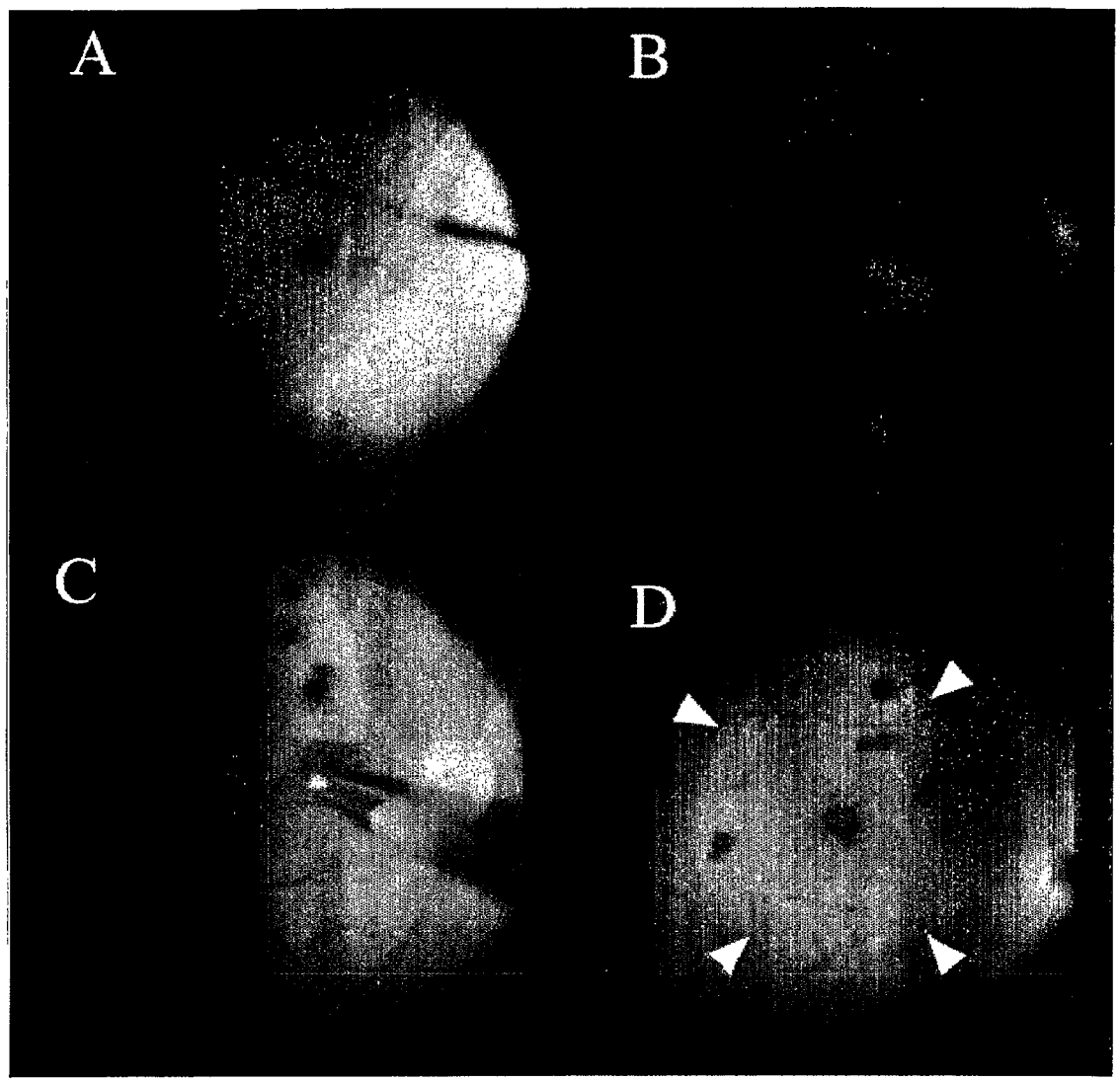
FIG. 6 shows photographs showing BBG-assisted ILM peeling for MH.
Figure 7:
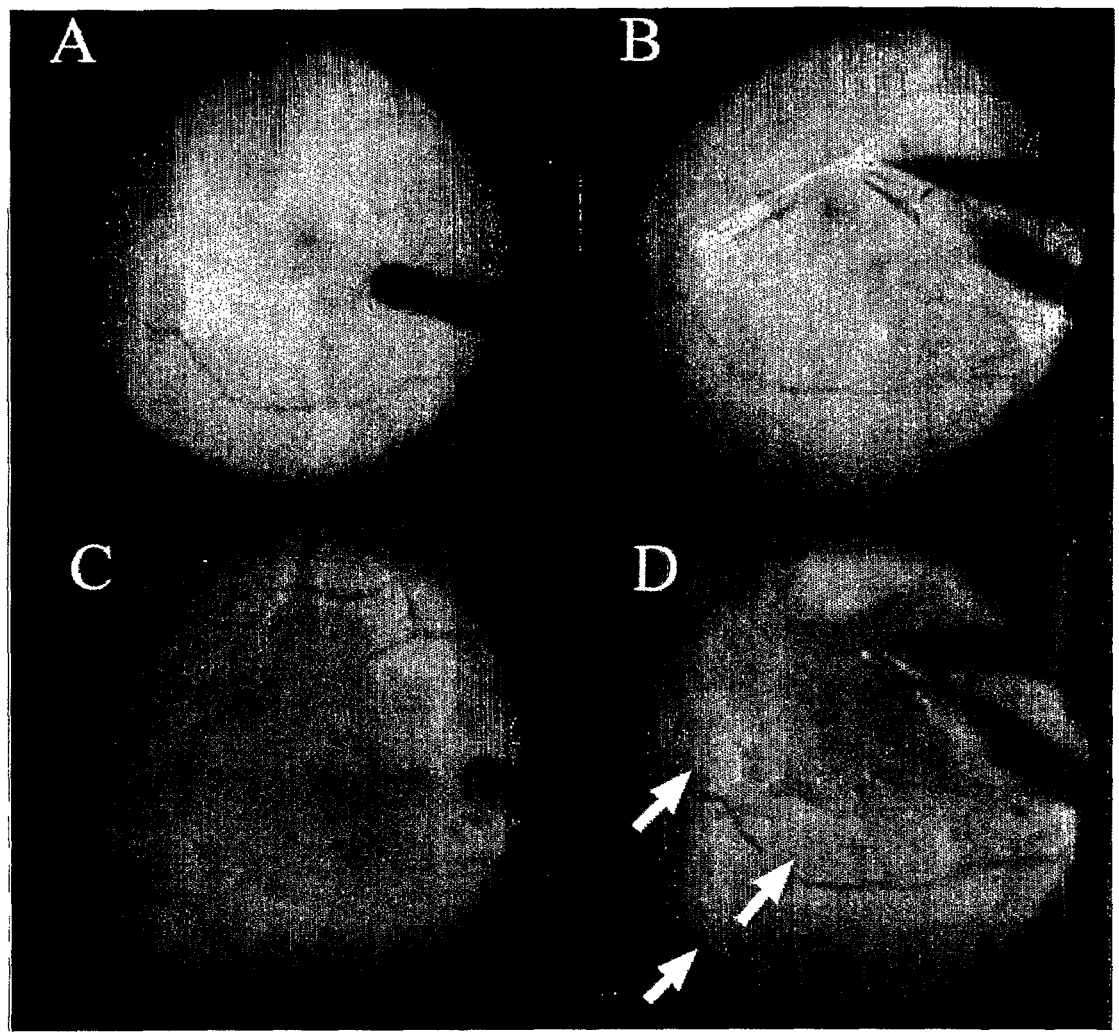
FIG. 7 shows a photography showing BBG-assisted membrane peeling for ERM.

Standard phacoemulsification was performed when needed. Surgery consisted of a three port pars plana vitrectomy with induction of a posterior vitreous detachment (PVD) by suction with a vitrectomy cutter using triamcinorone acetonide injection (Kenakolt-A® Bristol Pharmaceuticals KK, Tokyo, Japan) as required. BBG (Brilliant Blue G 250; Sigma-Aldrich, St. Louis, USA) was dissolved in intraocular irrigating solution (OPEGUARD®-MA, Senjyu Pharmaceutical Co. Ltd., Osaka, Japan). The solution was then sterilized through a 0.22 μm syringe filter. The final concentration of BBG was 0.25 mg/ml (289 mOsm, pH=7.44). The prepared BBG solution (0.5 ml) was then injected gently into the vitreous cavity (FIG. 6A) and washed out immediately with balanced salt solution (BSS Plus (Registered trademark), Santen, Osaka, Japan). In MH cases, the ILM was stained a bright blue color instantly. Removal of the ILM was performed using ILM forceps (FIGS. 6B, C). Following the removal of the ILM, the difference in the retinal surface color between the area from which the ILM had been removed and the surrounding area was clearly visible (FIG. 6D). In ERM cases however, staining of the ERM could not be confirmed at this concentration (FIG. 7A). After ERM peeling (FIG. 7B), BBG solution was injected again, followed by immediate irrigation of the vitreous cavity. The ILM of the area where the ERM had been removed was well stained with BBG (FIG. 7C). However, the area where residual ERM and posterior vitreous remained was not stained. The well-stained ILM could be easily removed with unstained residual ERM and posterior vitreous (FIG. 7D).

Finally, intraocular lenses were inserted in all cases. In MH cases, fluid-gas exchange was performed and was replaced with 15% sulfur hexafluoride gas. Patients were advised to maintain a face-down posture for one week.

Figure 8:
FIG. 8 shows transmission electron microscopic photography of the ILM.

The ILM including the ERM was removed from all 20 eyes successfully during surgery. Transmission electron microscopic examinations confirmed the presence of the ILM in all processed specimens (n=4) (FIG. 8). Postoperatively, any acute toxicity induced by BBG injection, such as a corneal edema, severe retinal edema and severe intraocular inflammation such as endophthalmitis, was not observed by slitlamp microscopy and opthalmoscopy examinations by day 14.

All MH cases were completely closed anatomically with both opthalmoscopy and OCT examinations. The preoperative median BCVA was 20/100 (range; 20/200-20/50). The postoperative median BCVA was 20/32 (range; 20/200-20/20). Visual acuity improved in 9 eyes (90%) by 2 or more Snellen lines and was unchanged in one eye. In two cases, complications included iatrogenic peripheral retinal breaks, which were treated by endolaser photocoagulation intraoperatively. Only one case of MH had an elevation of IOP (26 mmHg) after 6 months and this was treated with latanoprost. (Table 3)

In ERM surgery cases, the mean foveal thickness of retina measured with OCT decreased from 454.7±141.3 μm (preoperative) to 249.4±71.3 μm (postoperative). The postoperative BCVA (20/100-20/12.5; median: 20/32) was better than the preoperative BCVA (20/100-20/40; median: 20/50) in ERM cases (Table 4). Eight patients (80%) had an improvement of 2 or more lines on the Snellen chart, whereas the BCVA remained the same or improved by 1 line for the other two patients. The only complication was the protraction of vitreous hemorrhage in one case, which was absorbed after observation. No other adverse effects such as retinal pigment epithelium (RPE) atrophy were observed during the follow-up period in all cases.

TABLE 3

| Case No./Age.y/sex | MH stage | Preop. BCVA | Postop. BCVA | ILM peel | Postop. Retinal status | Lens status Preop./postop. | Postop. LOP elevation | complications | Follow Up (months) |
|---|---|---|---|---|---|---|---|---|---|
| 1/58/F | 3 | 20/63 | 20/20 | + | MH closed | Phakic/IOL | — | none | 9 |
| 2/77/M | 4 | 20/200 | 20/200 | + | MH closed | Phakic/IOL | — | none | 8 |
| 3/57/F | 3 | 20/50 | 20/32 | + | MH closed | Phakic/IOL | — | none | 7 |
| 4/62/F | 2 | 20/100 | 20/25 | + | MH closed | Phakic/IOL | — | none | 7 |
| 5/68/M | 3 | 20/100 | 20/40 | + | MH closed | Phakic/IOL | — | Peripheral retinal break | 7 |
| 6/79/M | 3 | 20/80 | 20/50 | + | MH closed | IOL/IOL | — | Peripheral retinal break | 7 |
| 7/78/M | 3 | 20/125 | 20/25 | + | MH closed | Phakic/IOL | — | none | 7 |
| 8/63/F | 3 | 20/50 | 20/20 | + | MH closed | Phakic/IOL | — | none | 7 |
| 9/64/F | 2 | 20/63 | 20/25 | + | MH closed | Phakic/IOL | — | none | 7 |
| 10/73/M | 4 | 20/200 | 20/50 | + | MH closed | Phakic/IOL | — | none | 6 |

Abbreviations of Table 3
MH: Macular hole,
BCVA: Best-corrected visual acuity,
preop.: Preoperation,
postop.: Postoperation,
IOL: Intraocular lens,
IOP: Intra ocular pressure

TABLE 4

| Case No./Age.y/sex | ERM status | Preop. BCVA | Postop. BCVA | ILM peel | Retinal thickness preop./postop. (μm) | Lens status Preop./postop. | Postop. LOP elevation | complications | Follow UP (months) |
|---|---|---|---|---|---|---|---|---|---|
| 1/33/M | 3 | 20/63 | 20/20 | + | 759/232 | IOL/IOL | — | none | 9 |
| 2/85/M | 4 | 20/200 | 20/200 | + | 441/248 | Phakic/IOL | — | none | 9 |
| 3/72/F | 3 | 20/50 | 20/32 | + | 423/354 | Phakic/IOL | — | none | 8 |
| 4/85/M | 2 | 20/100 | 20/25 | + | 478/266 | Phakic/IOL | — | Vitreous bleeding | 8 |
| 6/66/F | 3 | 20/100 | 20/40 | + | 501/240 | Phakic/IOL | — | none | 7 |
| 6/72/M | 3 | 20/80 | 20/50 | + | 417/190 | Phakic/IOL | — | none | 7 |
| 7/63/F | 3 | 20/125 | 20/25 | + | 429/232 | Phakic/IOL | — | none | 7 |
| 8/69/F | 3 | 20/50 | 20/20 | + | 556/382 | Phakic/IOL | — | none | 6 |
| 9/56/M | 2 | 20/63 | 20/25 | + | 228/146 | Phakic/IOL | — | none | 6 |
| 10/60/F | 4 | 20/200 | 20/50 | + | 315/204 | IOL/IOL | — | none | 6 |

Abbreviations of Table 4
ERM: Epiretinal membrane,
MH: Macular hole,
BCVA: Best-corrected visual acuity,
preop.: Preoperation,
postop.: Postoperation,
IOL: Intraocular lens,
IOP: Intra ocular pressure Example 4

4. The Biocompatibility of BBG

Preclinical Study of BBG as an Adjunct for Capsular Staining

4.1. Capsular Staining Ability of BBG

The capsular staining ability of BBG was assessed in pig eyes using graded concentrations of the dye.

The pig eyes were obtained from a local slaughterhouse and transported to the laboratory on ice. The extraocular muscles and other connective tissues were carefully cut off and the eyes were placed on the operation chamber. The BBG solution was prepared using the following method. Twenty milligrams of BBG (Coomassie. brilliant blue G 250; Signa-Aldrich, St. Louis, USA) were dissolved in 10 ml of intraocular irrigating solution (OPEGUARD.-MA, Senjyu Pharmaceutical Co., Ltd., Osaka, Japan) and sterilized with a syringe filter (Minisart. Sartorius AG, Goettingen, Germany). Under the operation microscope, the capsular staining by BBG was examined as follows. The anterior chamber was entered through the clear cornea with a 26-gauge needle mounted on a syringe. BBG was injected onto the anterior capsular through a 26-gauge needle introduced through the same entry (10, 1, 0.5, 0.25, 0.1 and 0.01 mg/ml). The anterior chamber was immediately irrigated by enhanced balanced salt solution (BSS Plus®, Santen Pharmaceuticals, Japan) and the excessive dye was easily washed out.

To deepen the anterior chamber, 1% sodium hyaluronate (Healon®, Pharmacia, Uppsala, Sweden) was injected. A CCC was initiated by preparing a small triangular anterior capsular flap with a bent 26-gauge disposable needle mounted on a viscoelastic syringe. The CCC was completed using a cystotome or capsulorhexis forceps.

Figure 9:
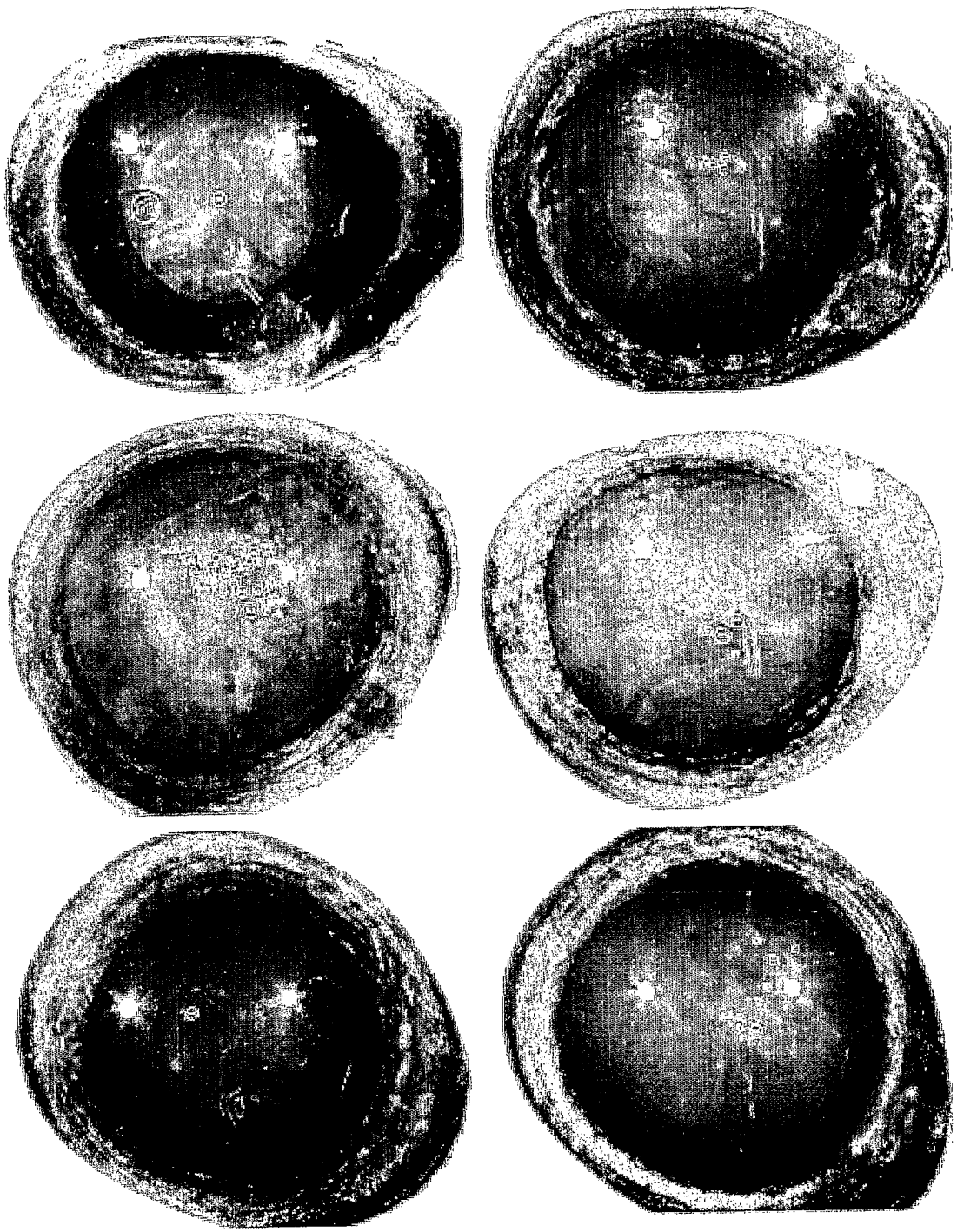
FIG. 9 shows the representative biomicroscopic images of BBG capsular staining. (original magnification ×4)

The dye stained the anterior capsule homogenously, and the edge of the CCC was clearly recognized under the operation microscope. The staining deepened as the concentration of the dye increased (0.25 mg/ml to 1 mg/ml, FIG. 9), and the minimal concentration needed to produce high quality staining with clear visualization was found to be 0.25 mg/ml (FIG. 9, top right). At 0.1 mg/ml and 0.01 mg/ml, the capsular staining was obscure, and no merit could be found in using the dye. (FIG. 9, middle left and bottom left). The side-port was also stained by the anterior chamber injection.

4.2. The Biocompatibility of BBG

Brown Norway rats (Kyudo, Fukuoka, Japan), postnatal 8 weeks, were studied as follows. The rats were anesthetized with an intraperitoneal injection of pentobarbital and their pupils were dilated with topical 1% tropicamide and 2.5% phenylephrine hydrochloride. The anterior chamber was entered through the clear cornea with a 30-gauge needle mounted on a syringe. Then a single anterior chamber injection was performed with each dye, BBG (10, 1, 0.5, 0.25, 0.1 and 0.01 mg/ml), ICG (5 mg/ml), trypan blue (1 mg/ml), and the control OPEGUARD. solution (n=6 for each dye, total 54 eyes). The mean osmolality and pH of each solution are shown in Table 1.

The dye remained in the anterior chamber and was followed by biomicroscopic examination for 2 months. The eyes were enucleated at 2 weeks and 2 months after operation. The eyes were analyzed by light microscopy, transmission and scanning electron microscopy.

4.3. Light Microscopy

The eyes were fixed in 4% paraformaldehyde and cut in half, embedded in paraffin, deparaffinized in xylene, rehydrated in ethanol, and washed in phosphate-buffered saline (PBS). The 4 µm thick sections were stained by hematoxylin and eosin, and observed by light microscope.

Figure 10:
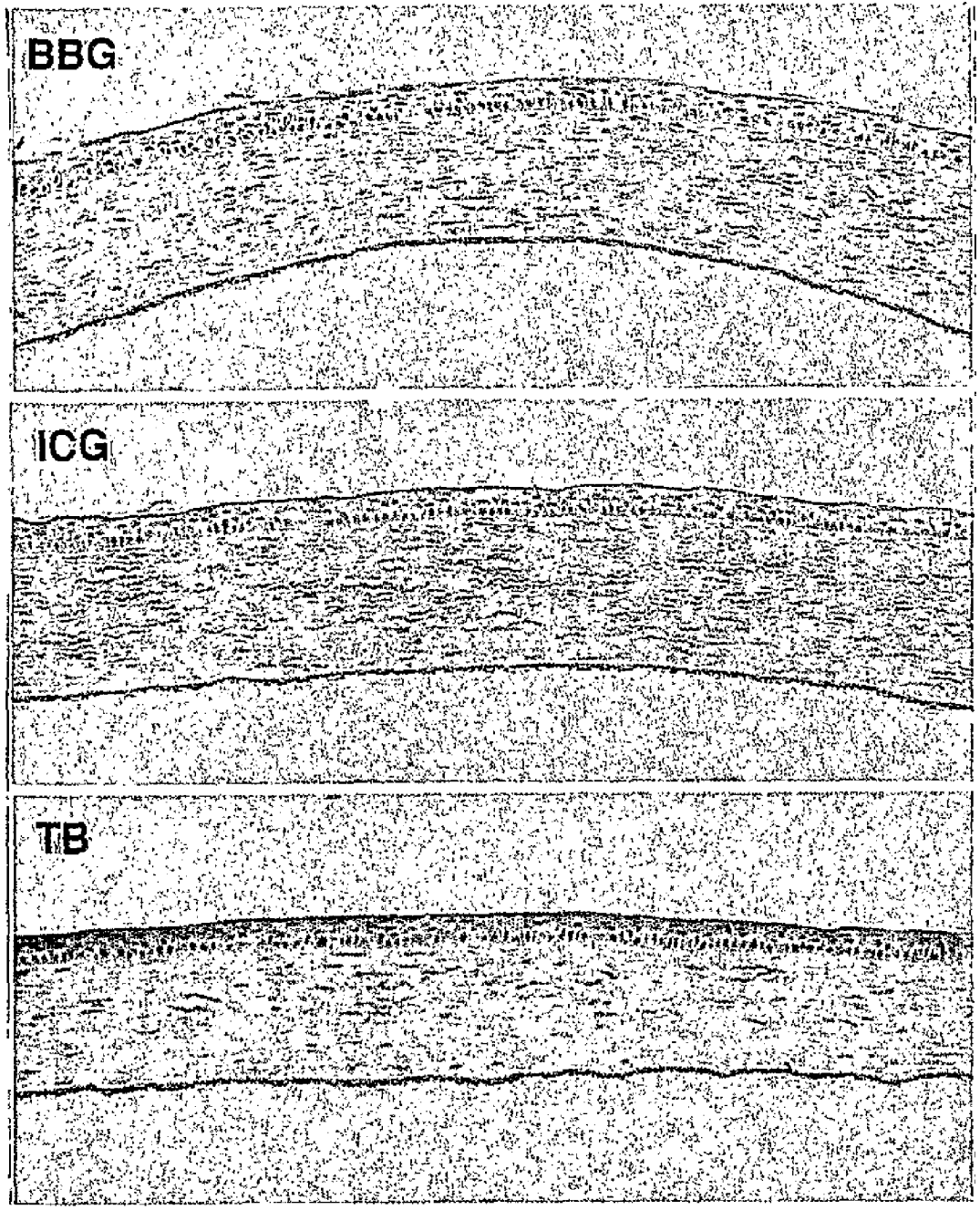
FIG. 10 shows hematoxilin and eosin stained sections of the cornea after anterior chamber injection of the dyes. (original magnification ×400).

Hematoxilin and eosin stained sections of the cornea showed no remarkable changes in each group (BBG, ICG, TB; FIG. 10). In the light microscopic examination, no signs of endothelial cell loss or corneal edema were observed. The lamellar collagen layers, stromal cells and epithelial cell layer were well preserved. No inflammatory cell infiltration was observed in all corneal layers.

4.4. TdT-dUTP Terminal Nick-End Labeling (TUNEL)

Apoptotic cell death was detected by TdT-dUTP Terminal Nick-End Labeling (TUNEL). Four micron-thick sections were made from samples fixed in 4% paraformaldehyde and embedded in paraffin. TUNEL staining was performed with the ApopTag®Fluorescein Direct in situ Apoptosis Detection Kit (Intergen Company, New York, N.Y.) according to the manufacturer's protocols. The sections were co-stained with propidium iodide (Molecular Probes, Eugene, Oreg.), thus allowing the observation of the cell nuclei by a fluorescence microscope (Olympus, Tokyo). Ten sections for each eye specimen were randomly selected and observed (n=3). The results are presented as the means±standard deviations.

Figure 11:
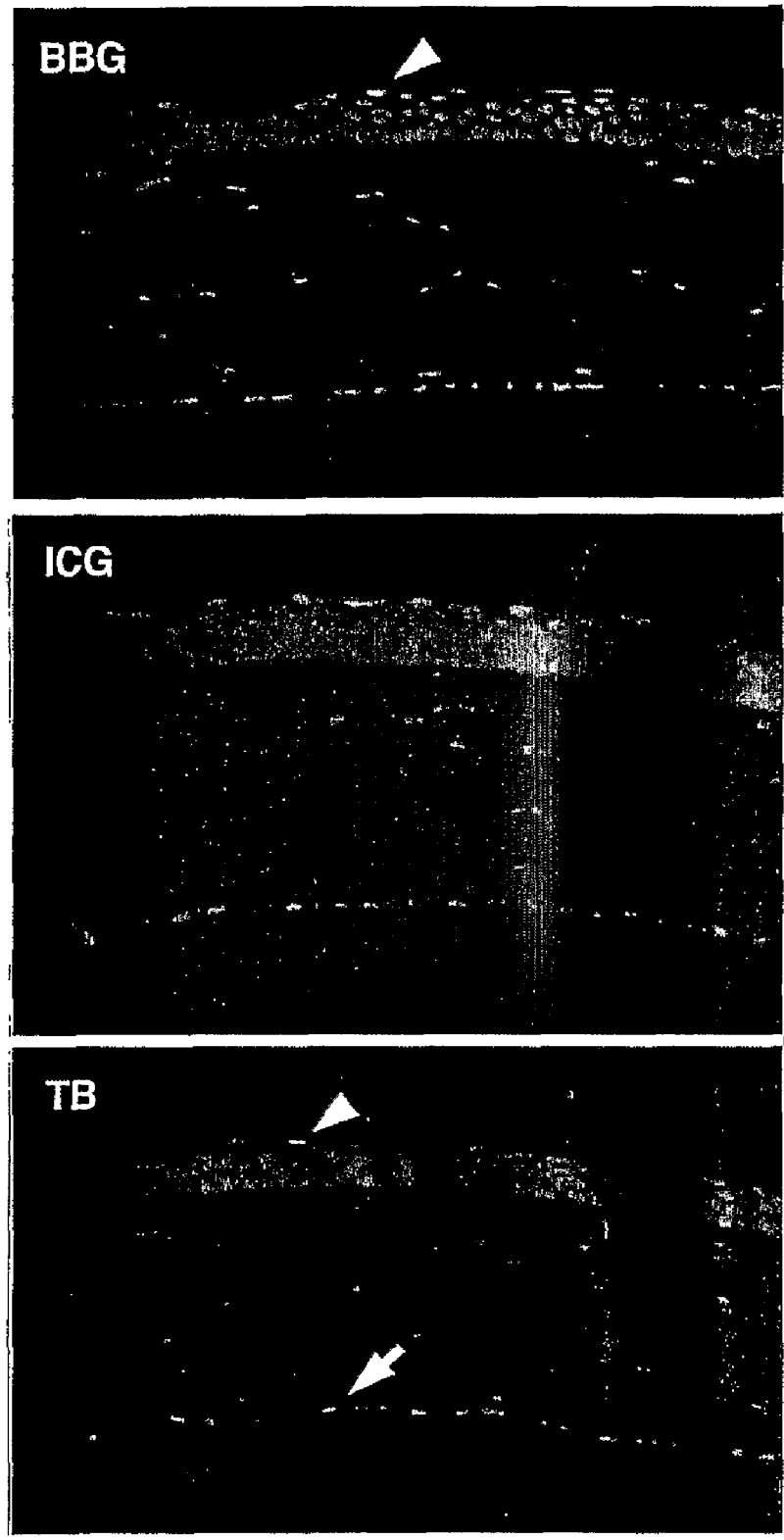
FIG. 11 shows photographs showing apoptotic cell death detected by TUNEL.

In all groups, apoptotic cell death of the corneal epithelium due to physiological turnover was observed occasionally (FIG. 11, arrowheads). In BBG groups, no TUNEL staining was observed in the corneal stromal cells, endothelium, ciliary body, and lens cells (FIG. 11). In the ICG group, no apparent apoptotic cell death was detected in 5 mg/ml concentration. In the TB group, apoptotic cell death of corneal endothelium was detected in 2% of the total endothelial cells. The other cells in the TB group did not undergo apoptotic cell death.

4.5. Transmission Electron Microscopy (TEM)

The eyes were enucleated and the anterior segments were fixed in 1% glutaraldehyde and 1% paraformaldehyde in PBS. The specimens were postfixed in veronal acetate buffer osmium tetroxide (2%), dehydrated in ethanol and water, and embedded in Epon. Ultrathin sections were cut from blocks and mounted on copper grids. The specimens were observed with a JEM 100CX electron microscope (JEOL, Tokyo).

Figure 12:
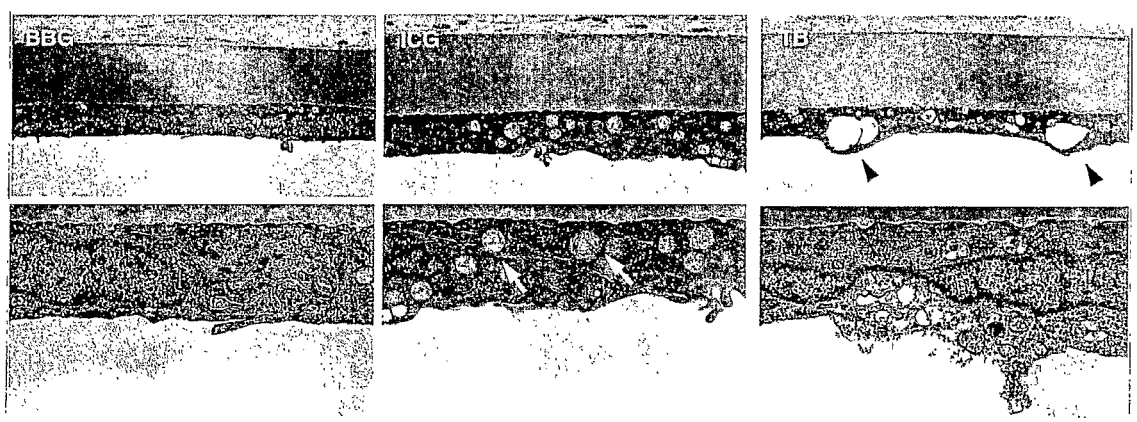
FIG. 12 shows photographs showing ultrastructure of the corneal cells and collagen cellular matrix by transmission electron microscopy.

In the BBG group, the ultrastructure of the corneal cells and collagen cellular matrix was well preserved in the highest concentration of 10 mg/ml (FIG. 12, left). In the corneal endothelium, cellular membranes, well defined nuclei, and cytoplasmic organelle showed no degenerative changes (FIG. 12, bottom left). The ICG group showed well preserved structure of endothelial cells, but some endothelial cells demonstrated signs of mitochondrial swelling (FIG. 12, middle, arrows). The TB group showed cyst formation in the endothelial cell layer due to separation between the cells (FIG. 12, right), and occasional degeneration of corneal endothelium in a patchy fashion (FIG. 12, bottom right).

4.6. Scanning Electron Microscopy (SEM)

The eyes were enucleated and the anterior segments fixed in 1% glutaraldehyde and 1% paraformaldehyde in PBS. The specimens were post-fixed in veronal acetate buffer osmium tetroxide (2%), and dehydrated in ethanol and water. The specimens were saturated in t-butyl alcohol, and critical point drying was performed (Eiko, Tokyo). The specimens were then placed on stubs by means of self-adhering carbon tabs and sputtered with Au of 20 nm thickness by argon plasma coater (Eiko). Next, the endothelial surface of the cornea was studied with a JEM 840 scanning electron microscope (JEOL).

Figure 13:
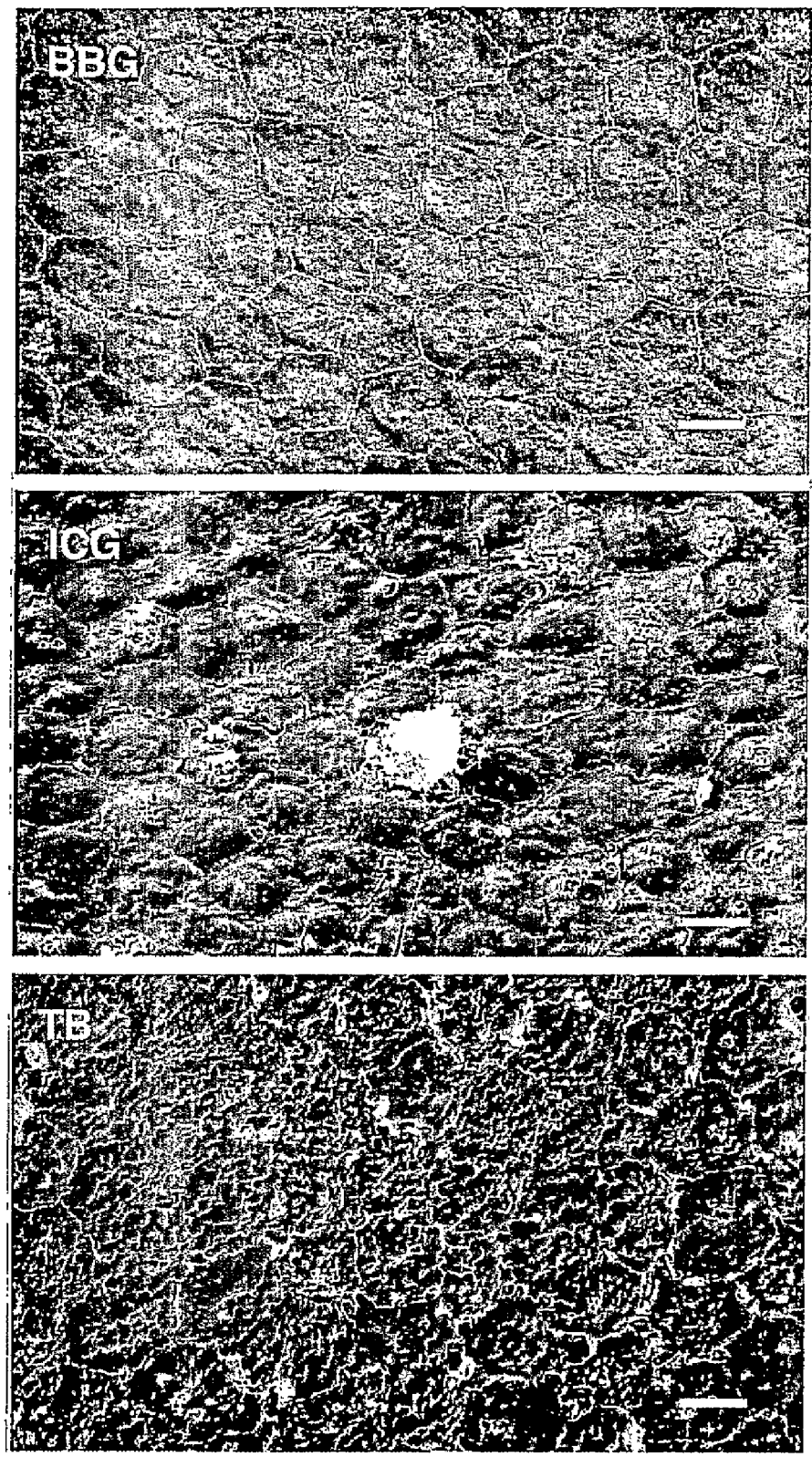
FIG. 13 shows photographs showing ultrastructure of corneal endothelial cells by scanning electron microscopy.

In the BBG exposed corneas, SEM showed normal cells similar to those in the controls. The SEM image demonstrated a normal hexagonal endothelial cell sheet with intact borders and no endothelial swelling (FIG. 13, top). The ICG group also showed some cellular swellings in the corneal endothelial sheet. Occasionally, degenerated endothelial cells were observed to be free from the original location. In the TB group, endothelial cell shrinkage was recognized in the central area of the cornea. The cell shrinkage led to endothelial cell loss in a sporadic fashion.

Example 5

5. Brilliant Blue-Assisted Continuous Curvilinear Capsulorhexis

As stated above, the inventors reported the results of a preclinical study involving a new dye, Brilliant Blue G (BBG), which stained the anterior capsule at lower concentrations and with minimal toxicity. This example demonstrates the efficacy of BBG in capsular staining of a human eye.

A 70-year-old woman with a white mature cataract underwent BBG-assisted CCC and phacoemulsification with intraocular lens (IOL) implantation in August 2004. The patient had no other ocular diseases, such as glaucoma, uveitis or corneal disorders. Coomassie® BBG 250 (Sigma-Aldrich, St. Louis, USA) was dissolved in intraocular irrigating solution (OPEGUARD®-MA; Senjyu Pharmaceutical Co., Ltd., Osaka, Japan) at a dose of 0.25 mg/ml and sterilized with a syringe filter. The BBG solution was gently injected into the anterior chamber and then washed out immediately with balanced salt solution (BSS).

Figure 14:
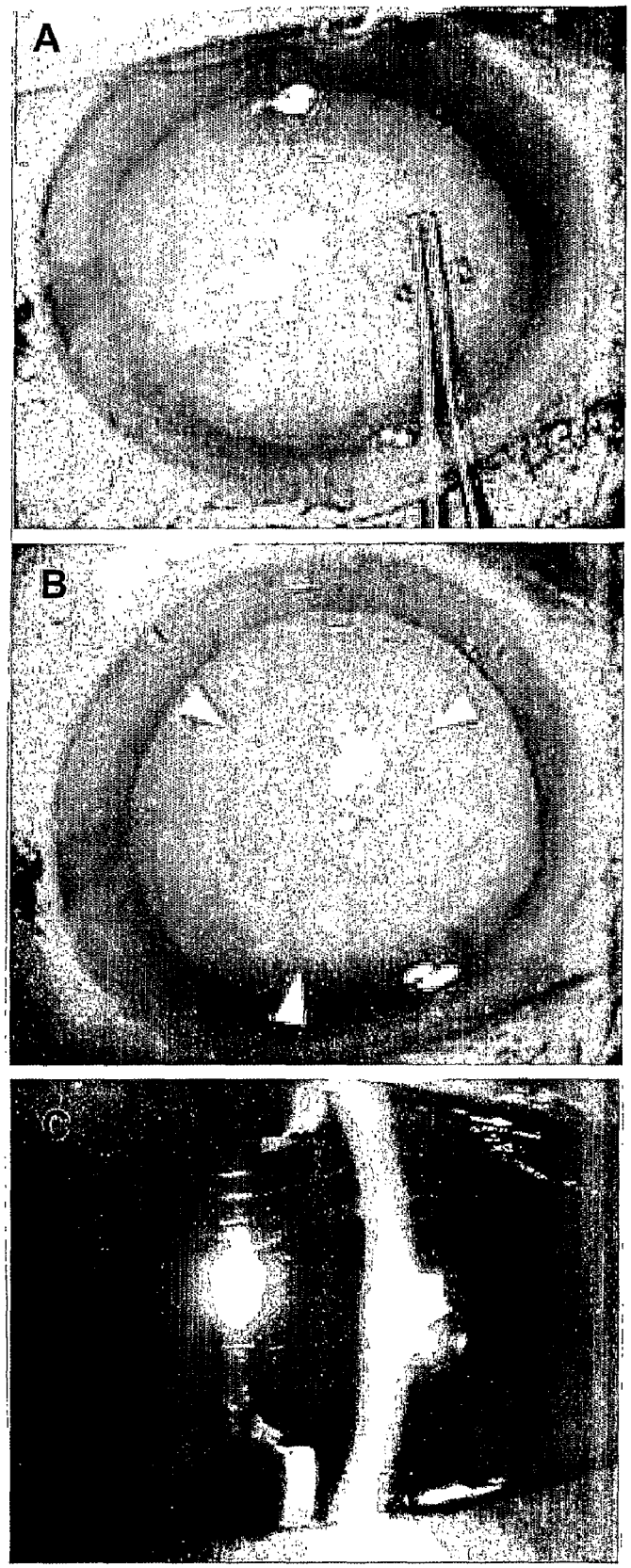
FIG. 14 shows photographs showing BBG-Assisted CCC.

According to FIG. 14, the bright blue anterior capsule was clearly visible during the surgical production of the CCC. BBG solution (0.25 mg/ml) was injected into the anterior chamber of the eye, which was immediately irrigated. (A) The arrow indicates the CCC created in the eye, which had a white cataract. (B) The arrowheads show the margins of the completed CCC. (C) After phacoemulsification and aspiration, an IOL was inserted. The following day, no acute toxicity (such as corneal edema, severe inflammation or elevated intraocular pressure) was observed. The patient's visual acuity improved from light perception (LP) to 20/20 and a minimal corneal endothelial cell loss of 0.8% was observed after 2 months.

This study was carried out with the approval of the Internal Review Board of our institution and was performed in accordance with the ethical standards laid down in the 1989 Declaration of Helsinki. The potential benefits and risks of the treatment were explained to the patient and her informed consent was obtained before surgery.

Other features and advantages of the invention will be apparent from the foregoing detailed description for persons with ordinary skill in the art. The terms and expression which have been employed are use as terms of description and are not intended to be limiting, but it is recognized that various modifications are possible within the scope of the claimed invention.

The invention claimed is:

1. A method for staining and removing an ophthalmic membrane comprising:
    preparing a staining composition, the staining composition comprising a Brilliant Blue G (BBG), a pharmaceutically acceptable salt of BBG or a hydrate of BBG, as a primary component;
    staining the ophthalmic membrane by using a predetermined concentration of the staining composition; and
    peeling the stained membrane.

2. The method of claim 1, wherein the predetermined concentration of the staining composition is in the range of 0.1 mg/ml to 10 mg/ml of BBG, a pharmaceutically acceptable salt of BBG or a hydrate of BBG.

3. The method of claim 1, wherein the predetermined concentration of the staining composition is in the range of 0.1 mg/ml to 1.0 mg/ml of BBG, a pharmaceutically acceptable salt of BBG or a hydrate of BBG.

4. The method of claim 1, wherein the predetermined concentration of the staining composition is in the range of 0.1 mg/ml to 0.25 mg/ml of BBG, a pharmaceutically acceptable salt of BBG or a hydrate of BBG.

5. The method of claim 1, wherein the ophthalmic membrane is an internal limiting membrane (ILM).

6. The method of claim 1, wherein the ophthalmic membrane is an anterior capsule.

* * * * *